(12) United States Patent
Kubota et al.

(10) Patent No.: US 10,098,542 B2
(45) Date of Patent: Oct. 16, 2018

(54) FUNDUS OBSERVATION APPARATUS

(71) Applicant: KABUSHIKI KAISHA TOPCON, Itabashi-ku (JP)

(72) Inventors: Atsushi Kubota, Itabashi-ku (JP); Yusuke Ono, Kita-ku (JP); Shigetaka Tsuri, Itabashi-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 15/244,710

(22) Filed: Aug. 23, 2016

(65) Prior Publication Data

US 2016/0360963 A1 Dec. 15, 2016

Related U.S. Application Data

(62) Division of application No. 14/377,082, filed as application No. PCT/JP2012/071544 on Aug. 27, 2012, now Pat. No. 9,560,964.

(30) Foreign Application Priority Data

Feb. 28, 2012 (JP) ................................. 2012-041517
Apr. 27, 2012 (JP) ................................. 2012-103942

(51) Int. Cl.
*G06K 9/00* (2006.01)
*A61B 3/12* (2006.01)
(Continued)

(52) U.S. Cl.
CPC .......... *A61B 3/1233* (2013.01); *A61B 3/0025* (2013.01); *A61B 3/0041* (2013.01);
(Continued)

(58) Field of Classification Search
CPC ..... A61B 3/0025; A61B 3/0041; A61B 3/102; A61B 3/1233; A61B 3/1241; A61B 3/145;
(Continued)

(56) References Cited

U.S. PATENT DOCUMENTS 6,377,349 B1 4/2002 Fercher
2003/0156258 A1 8/2003 Tanassi et al.
(Continued)

FOREIGN PATENT DOCUMENTS

EP 2 147 634 A1 1/2010
JP 09 276232 10/1997
(Continued)

OTHER PUBLICATIONS

International Search Report dated Sep. 18, 2012 in PCT/JP12/071544 filed Aug. 27, 2012.
(Continued)

*Primary Examiner* — Nirav G Patel
(74) *Attorney, Agent, or Firm* — Oblon, McClelland, Maier & Neustadt, L.L.P.

(57) ABSTRACT

Distribution information of examination results of eye fundus is displayed. An imaging part carries out movie imaging of fundus. A tomographic image forming part comprises an optical system that generates and detects interference light by superposing signal light from fundus on reference light and a scanner that scans fundus with signal light, and forms tomographic image of fundus based on detection results of interference light acquired by the scanning. A setting part sets scan-target location of signal light on distribution information. A specifying part specifies image region in fundus image obtained by the movie imaging that corresponds to the scan-target location. A controller controls the scanner based on the specified image region to carry out scanning of
(Continued)

signal light. The tomographic image forming part forms tomographic image from the detection results of interference light acquired by the scanning of signal light based on the control.

11 Claims, 13 Drawing Sheets

(51) Int. Cl.
    *A61B 3/10*     (2006.01)
    *G06T 1/00*     (2006.01)
    *A61B 3/00*     (2006.01)
    *G06T 7/00*     (2017.01)
    *A61B 3/14*     (2006.01)

(52) U.S. Cl.
    CPC .............. *A61B 3/102* (2013.01); *A61B 3/145* (2013.01); *G06T 1/0007* (2013.01); *G06T 7/0012* (2013.01); *A61B 3/1241* (2013.01); *G06T 2207/10101* (2013.01); *G06T 2207/30041* (2013.01)

(58) Field of Classification Search
    CPC ......... G06T 1/0007; G06T 2207/10101; G06T 2207/30041; G06T 7/0012
    See application file for complete search history.

(56) References Cited

U.S. PATENT DOCUMENTS

| | | |
|---|---|---|
| 2004/0102682 A1 | 5/2004 | Zahlmann et al. |
| 2008/0100612 A1 | 5/2008 | Dastmalchi |
| 2009/0033870 A1 | 2/2009 | Hangai et al. |
| 2009/0190092 A1 | 7/2009 | Tsukada et al. |
| 2010/0149489 A1 | 6/2010 | Kikawa et al. |
| 2014/0078466 A1 | 3/2014 | Sekine |

FOREIGN PATENT DOCUMENTS

| | | |
|---|---|---|
| JP | 11 325849 | 11/1999 |
| JP | 2002 139421 | 5/2002 |
| JP | 2003 235800 | 8/2003 |
| JP | 2006 507068 | 3/2006 |
| JP | 2007 024677 | 2/2007 |
| JP | 2008 073099 | 4/2008 |
| JP | 2008 237237 | 10/2008 |
| JP | 2008 259544 | 10/2008 |
| JP | 2009 34480 | 2/2009 |
| JP | 2010 227610 | 10/2010 |

OTHER PUBLICATIONS

Extended European Search Report dated Sep. 15, 2015 in Patent Application No. 12869703.4.

FUNDUS OBSERVATION APPARATUS

CROSS-REFERENCE TO RELATED APPLICATIONS

This application is a divisional of U.S. Ser. No. 14/377,082 filed Aug. 6, 2014, which is the national stage of PCT/JP2012/071544 filed Aug. 27, 2012, and which claims priority to JP 2012-103942 filed Apr. 27, 2012 and JP 2012-041517 filed Feb. 28, 2012. The entire content of U.S. application Ser. No. 14/377,082 is incorporated herein by reference.

TECHNICAL FIELD

The present invention relates to a fundus observation apparatus that obtains an image of an eye fundus by using optical coherence tomography (OCT).

BACKGROUND TECHNOLOGY

In recent years, OCT that forms images of the surface morphology and internal morphology of an object by using a light beam from a laser light source or the like has attracted attention. Unlike an X-ray CT apparatus, optical coherence tomography is noninvasive to human bodies, and is therefore expected to be utilized in the medical field and biological field. For example, in the ophthalmology, apparatuses that form images of a fundus and cornea or the like are in a practical stage.

The apparatus disclosed in Patent Document 1 uses a technique of so-called "Fourier Domain OCT." That is to say, the apparatus irradiates a low-coherence light beam to an object, superposes the reflected light and the reference light to generate an interference light, and acquires the spectral intensity distribution of the interference light to execute Fourier transform, thereby imaging the morphology in the depth direction (the z-direction) of the object. Furthermore, the apparatus is provided with a galvano mirror that scans a light beam (signal light) along one direction (x-direction) perpendicular to the z-direction, and is thereby configured to form an image of a desired measurement target region of the object. An image formed by this apparatus is a two-dimensional tomographic image in the depth direction (z-direction) along the scanning direction (x-direction) of the light beam. The technique of this type is also called Spectral Domain.

Patent Document 2 discloses a technique of scanning with a signal light in the horizontal direction (x-direction) and the vertical direction (y-direction) to form multiple two-dimensional tomographic images in the horizontal direction, and acquiring and imaging three-dimensional tomographic information of a measured range based on the tomographic images. As the three-dimensional imaging, for example, a method of arranging and displaying multiple tomographic images in the vertical direction (referred to as stack data or the like), or a method of executing a rendering process on volume data (voxel data) based on stack data to form a three-dimensional image may be considered.

Patent Documents 3 and 4 disclose other types of OCT apparatuses. Patent Document 3 describes an OCT apparatus that images the morphology of an object by sweeping the wavelength of light that is irradiated to an object (wavelength sweeping), detecting interference light obtained by superposing the reflected lights of the light of the respective wavelengths on the reference light to acquire its spectral intensity distribution, and executing Fourier transform. Such an OCT apparatus is called a Swept Source type or the like. The Swept Source type is a kind of the Fourier Domain type.

Patent Document 4 discloses an example of applying OCT to the ophthalmologic field. It should be noted that, before OCT was applied, a retinal camera, a slit lamp microscope, etc. were used as apparatuses for observing an eye (e.g., see Patent Documents 5 and 6). The retinal camera is an apparatus that photographs the fundus by projecting illumination light onto the eye and receiving the reflected light from the fundus. The slit lamp microscope is an apparatus that obtains an image of the cross-section of the cornea by cutting off the light section of the cornea using slit light.

The apparatus with OCT is superior relative to the retinal camera, etc. in that high-definition images can be obtained, further in that tomographic images and three-dimensional images can be obtained, etc.

Thus, the apparatus using OCT can be used for observation of various regions of the eye and is capable of obtaining high-definition images, and therefore, has been applied to the diagnosis of various ophthalmic disorders.

PRIOR ART DOCUMENTS

Patent Documents

[Patent Document 1]
 Japanese Unexamined Patent Application Publication No. H11-325849
[Patent Document 2]
 Japanese Unexamined Patent Application Publication No. 2002-139421
[Patent Document 3]
 Japanese Unexamined Patent Application Publication No. 2007-24677
[Patent Document 4]
 Japanese Unexamined Patent Application Publication No. 2008-73099
[Patent Document 5]
 Japanese Unexamined Patent Application Publication No. H09-276232
[Patent Document 6]
 Japanese Unexamined Patent Application Publication No. 2008-259544

SUMMARY OF THE INVENTION

Problem that the Invention is to Solve

In eye fundus examinations, fluorescent imaging for comprehending the condition of blood vessels and the condition of blood flow has been carried out. Fluorescent imaging includes methods with a fluorescent agent (fluorescein, indocyanine green, etc.) and methods without a fluorescent agent (autofluorescent imaging).

Conventionally, in the case in which an image obtained by fluorescent imaging (referred to as a fluorescent image) and images obtained by OCT are compared and observed, the position in the fluorescent image corresponding to an abnormal site in the fluorescent image is specified by carrying out position matching between the fluorescent image and a fundus image photographed while OCT measurement, thereby carrying out display operation as if a tomographic image at the concerned location is acquired. That is, the conventional technology carries out the position matching between the fluorescent image and the tomographic image as a post-processing.

In contrast to such a present state, there has been a demand for actually carrying out OCT measurement of the abnormal site to acquire a tomographic image in order to comprehend the condition of the deep part of the abnormal site obtained from the fluorescent image. Moreover, since the above-mentioned post-processing must include the comparison between the fluorescent image and the fundus image, the post-processing is troublesome for the user.

Furthermore, there also has been a demand for determining a location to which OCT measurement is applied based on the result of an examination other than fluorescent imaging. Here, examinations other than fluorescent imaging include imaging for obtaining an image of an eye fundus and measurement for obtaining a functional state of an eye fundus (fundus function measurement). Images obtained by the imaging may include: a color fundus image; an SLO (Scanning Laser Ophthalmoscope) image; a three-dimensional image by OCT; a projection image obtained by integrating (projecting) this three-dimensional image in the z-direction; a shadowgram obtained by integrating (projecting) a part of the depth region of this three-dimensional image in the z-direction. Further, the fundus function measurement may include measurement methods for obtaining distribution of measured values over a fundus such as: the visual field test for measuring the area of visual field by using a perimeter; SLO microperimetry (SLO scotometry) for measuring the retinal sensitivity; layer thickness measurement for measuring the thickness of a layer in a fundus by using OCT or nerve-fiver-layer analyzing apparatus.

Similar to the case of fluorescent imaging, operations for setting a location to which OCT is applied based on the results of such examinations are troublesome.

The present invention is developed in order to solve the above problems, and its purpose is to provide technology that enables users to easily set measurement location for OCT of an eye fundus based on an examination result.

Means for Solving the Problem

In order to achieve the aforementioned purpose, the invention described in claim 1 is a fundus observation apparatus, comprising: a display configured to display distribution information of examination results of an eye fundus acquired by examination carried out in the past; an imaging part configured to carry out movie imaging of the eye fundus; a tomographic image forming part configured to comprise an optical system that generates and detects interference light by superposing signal light returned from the eye fundus on reference light, and a scanner that scans the eye fundus with the signal light, and further configured to form a tomographic image of the eye fundus based on the detection results of the interference light acquired by the scanning; a setting part configured to set a scan-target location of the signal light on the distribution information displayed on the display; a specifying part configured to specify an image region in a fundus image obtained by the movie imaging that corresponds to the scan-target location; and a controller configured to control the scanner based on the specified image region to carry out the scanning of the signal light, wherein the tomographic image forming part forms a tomographic image from the detection results of the interference light acquired by the scanning of the signal light based on the control.

The invention described in claim 2 is the fundus observation apparatus of claim 1, wherein the setting part comprises an analyzer configured to analyze the distribution information to specify a lesion candidate site in the eye fundus, and sets the scan-target location based on the specified lesion candidate site.

The invention described in claim 3 is the fundus observation apparatus of claim 2, wherein the analyzer comprises: a first storage configured to previously store two or more analysis programs corresponding to two or more types of the distribution information; a first type specifying part configured to specify the type of the distribution information displayed on the display; and a first selecting part configured to select an analysis program corresponding to the specified type from among the two or more analysis programs, and the analyzer analyzes the distribution information with the selected analysis program to specify the lesion candidate site.

The invention described in claim 4 is the fundus observation apparatus of claim 3, wherein the first type specifying part specifies the type of the distribution information based on the examination result of a characteristic site of the eye fundus in the displayed distribution information.

The invention described in claim 5 is the fundus observation apparatus of claim 3, wherein the displayed distribution information is associated with preset identification information indicating the type thereof in advance, and the first type specifying part specifies the type of the distribution information based on the identification information.

The invention described in claim 6 is the fundus observation apparatus of claim 1, wherein the distribution information includes an image of the eye fundus in which pixel values correspond to the examination results, the specifying part comprises: a second storage configured to previously store two or more image-analysis programs corresponding to two or more types of images; a second type specifying part configured to specify the type of the image displayed on the display; and a second selecting part configured to select an image-analysis program corresponding to the specified type from among the two or more image-analysis programs, and the specifying part carries out image matching between the displayed image and the fundus image with the selected image-analysis program, and specifies an image region in the fundus image that is associated, by the image matching, with the scan-target location in the displayed image.

The invention described in claim 7 is the fundus observation apparatus of claim 6, wherein the second type specifying part specifies the type of the displayed image based on the pixel values at a characteristic site of the eye fundus in the displayed image.

The invention described in claim 8 is the fundus observation apparatus of claim 6, wherein the displayed image is associated with preset identification information indicating the type thereof in advance, and the second type specifying part specifies the type of the displayed image based on the identification information.

The invention described in claim 9 is the fundus observation apparatus of claim 3, wherein the distribution information includes a fluorescent image of the eye fundus in which pixel values correspond to the examination results, and the types of the fluorescent image include a first type that is captured by applying a fluorescent agent and a second type that is captured without a fluorescent agent.

The invention described in claim 10 is the fundus observation apparatus of claim 1, wherein the distribution information include at least one of a fluorescent image, infrared image and red-free image of the eye fundus in which pixel values correspond to the examination results.

The invention described in claim 11 is the fundus observation apparatus of claim 1, further comprising an image storage configured to store a supplementary image of the eye fundus obtained together with the distribution information, wherein the setting part sets the scan-target location on the distribution information, the specifying part specifies an image region in the supplementary image corresponding to the scan-target location set on the distribution information, and specifies an image region in the fundus image corresponding to the image region specified in the supplementary image, the controller controls the scanner based on the image region specified in the fundus image to carry out the scanning of the signal light, and the tomographic image forming part forms a tomographic image from the detection results of the interference light acquired by the scanning of the signal light based on this control.

The invention described in claim 12 is the fundus observation apparatus of claim 11, wherein the distribution information includes measurement result information in which measured values obtained by carrying out measurement of the eye fundus correspond to the examination results, and the setting part sets the scan-target location on the measurement result information.

The invention described in claim 13 is the fundus observation apparatus of claim 12, wherein the measurement result information includes at least one of the measurement result of area of visual field obtained by visual field test, the measurement result of retinal sensitivity obtained by microperimetry, and the measurement result of thickness of a layer in an eye fundus obtained by layer thickness measurement.

The invention described in claim 14 is the fundus observation apparatus of claim 12, wherein the display displays the measurement result information over the supplementary information or the fundus image.

The invention described in claim 15 is the fundus observation apparatus of claim 12, wherein the distribution information includes an image of a different type from the supplementary information, and the setting part sets the scan-target location on this image.

The invention described in claim 16 is the fundus observation apparatus of claim 11, wherein the supplementary information and the fundus image are of the same type.

The invention described in claim 17 is the fundus observation apparatus of claim 1, wherein the setting part comprises an operation part configured to receive an operation for setting the scan-target location.

The invention described in claim 18 is the fundus observation apparatus of claim 17, wherein the display displays, over the distribution information, settable area information indicating an area in which the scan-target location may be set.

The invention described in claim 19 is the fundus observation apparatus of claim 18, further comprising a display controller configured to display the settable area information over the distribution information when an operation for setting the scan-target location inside the external region of the area in the distribution information is carried out.

The invention described in claim 20 is the fundus observation apparatus of claim 18, further comprising: a scan condition setting part configured to set a scan condition of the signal light; and a display controller configured to switch the form of the settable area information displayed over the distribution information depending on the setting result of the scan condition.

The invention described in claim 21 is the fundus observation apparatus of claim 18, wherein when an operation for setting the scan-target location inside the external region of the area in the distribution information is carried out, the setting part sets a new scan-target location inside the internal region of the area.

The invention described in claim 22 is the fundus observation apparatus claim 17, wherein the operation part comprises a first operation part configured to receive an operation for translating the scan-target location set on the displayed distribution information.

The invention described in claim 23 is the fundus observation apparatus of claim 17, wherein the operation part comprises a second operation part configured to receive an operation for rotating the scan-target location set on the displayed distribution information.

The invention described in claim 24 is the fundus observation apparatus of claim 17, wherein the operation part comprises at least one of a pointing device and a graphical user interface.

The invention described in claim 25 is the fundus observation apparatus of claim 1, wherein when the image region corresponding to the scan-target location is specified by the specifying part, the controller controls the display to display a still image based on a single frame of the fundus image and information indicating the image region specified in the single frame.

The invention described in claim 26 is the fundus observation apparatus of claim 25, wherein after the still image and the information are displayed, the specifying part carries out image matching between a new frame of the fundus image acquired by the imaging part at the time of this display process and the single frame to specify an image region in the new frame corresponding to the image region specified in the single frame, and the controller controls the scanner based on the image region specified in the new frame to carry out the scanning of the signal light.

The invention described in claim 27 is the fundus observation apparatus of claim 1, wherein the distribution information includes an image acquired by movie imaging or still imaging carried out by the imaging part in the past, or information generated from a tomographic image formed by the tomographic image forming part in the past.

Effect of the Invention

According to the present invention, when OCT measurement of an eye fundus is carried out based on an examination result, it is possible to easily carry out a setting work for the measurement location.

MODE FOR CARRYING OUT THE INVENTION

Examples of embodiments of a fundus observation apparatus according to the present invention will be described in detail with reference to the drawings. The fundus observation apparatus according to the present invention forms a tomographic image and/or a three-dimensional image of a fundus by using OCT. Images obtained by OCT are sometimes referred to as OCT images. Furthermore, a measuring action for forming an OCT image is sometimes referred to as OCT measurement. It should be noted that any of the contents described in the documents cited in this description may be applied to the following embodiments in an arbitrary way.

In the following embodiments, configurations in which Fourier Domain OCT is employed will be described in detail. Particularly, fundus observation apparatuses according to the following embodiments are capable of obtaining both a fundus OCT image with Spectral Domain OCT and a fundus image, which is similar to the apparatus disclosed in Patent Document 4. It should be noted that configurations according to the present invention may be applied to a fundus observation apparatus of any type other than Spectral Domain (for example, Swept Source OCT). Further, apparatuses in which an OCT apparatus and a retinal camera are combined are explained in the embodiments; however, it is possible to combine an OCT apparatus comprising configuration according to the embodiments with a fundus imaging apparatus of any type, such as an SLO, slit lamp microscope, ophthalmologic surgical microscope, etc.

First Embodiment

Configurations

Figure 1:
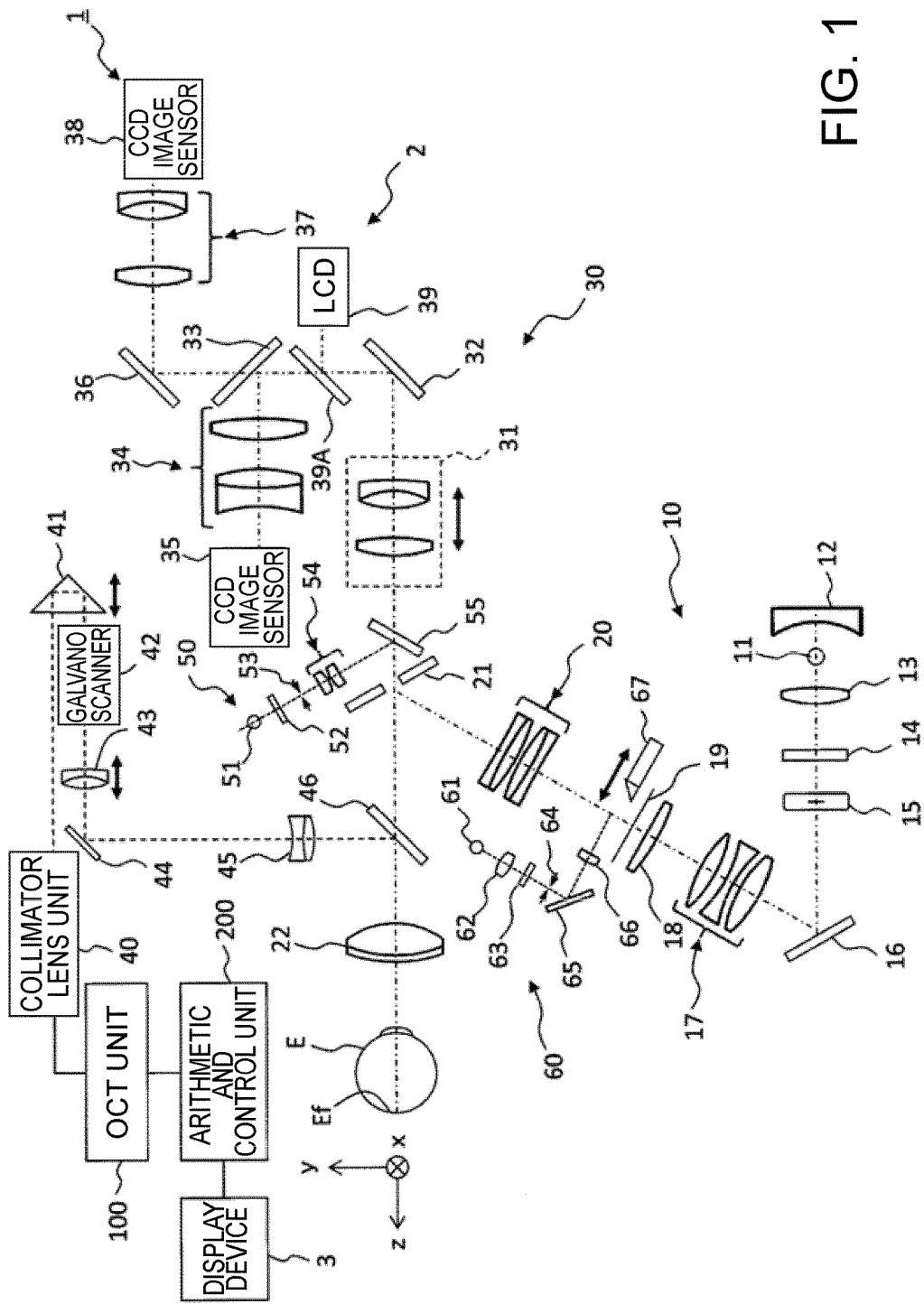
FIG. 1 is a schematic diagram showing an example of a configuration of a fundus observation apparatus according to an embodiment.
Figure 2:
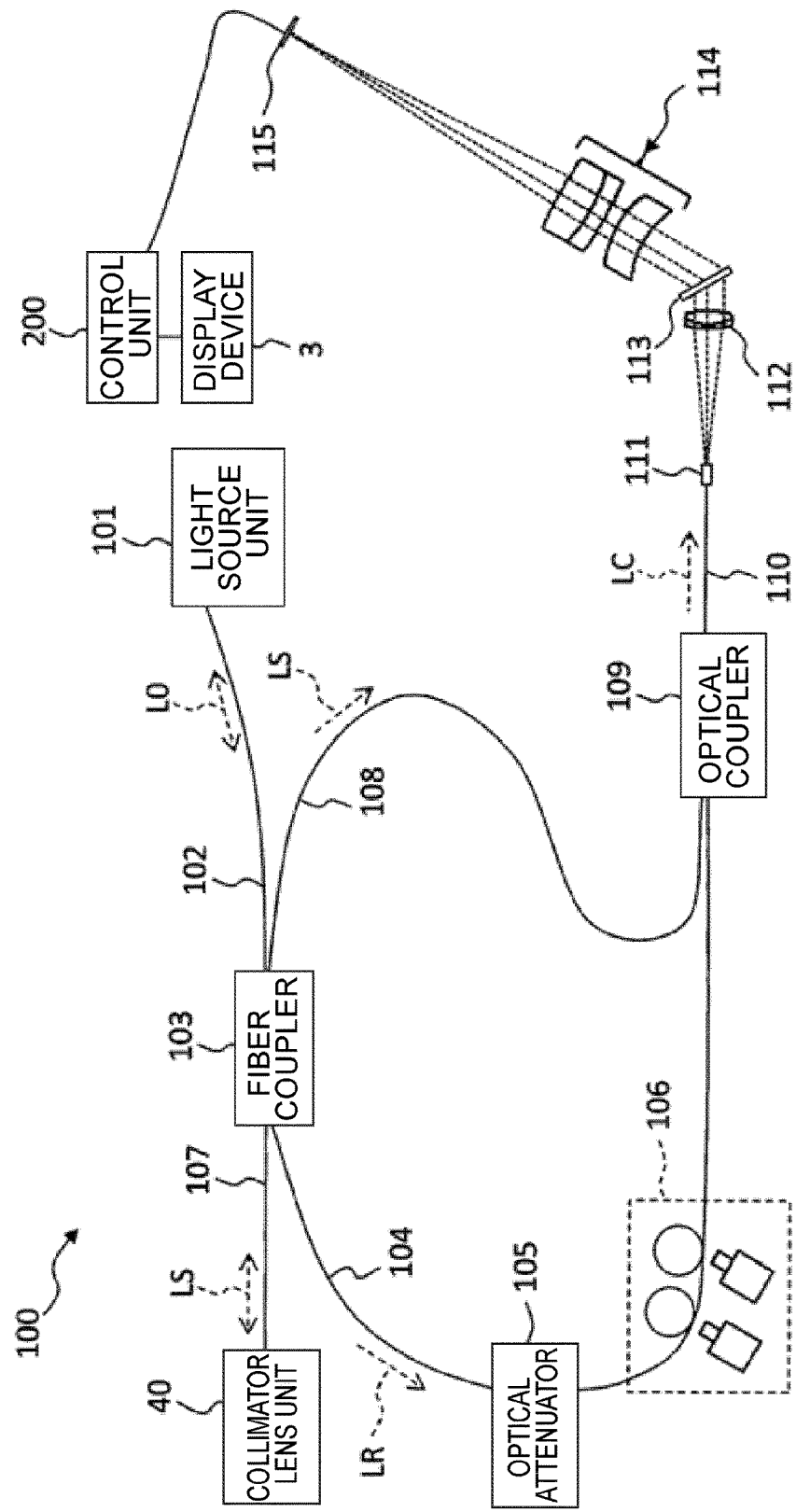
FIG. 2 is a schematic diagram showing an example of a configuration of a fundus observation apparatus according to an embodiment.

A fundus observation apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit 2 shown in FIG. 1 is provided with an optical system for forming a 2-dimensional image (fundus image) representing the surface morphology of the fundus Ef of an eye E. Fundus images include observation images, photographed images, etc. The observation image is, for example, a monochromatic moving image formed at a prescribed frame rate using near-infrared light. The observation image is an example of "fundus image" and the retinal camera unit 2 is an example of "imaging part". The photographed image may be, for example, a color image captured by flashing visible light, or a monochromatic still image captured by using near-infrared light or visible light as illumination light. The retinal camera unit 2 may also be configured to be capable of capturing other types of images such as a fluorescein angiography image, an indocyanine green fluorescent image, and an autofluorescent image. In such cases, an illumination optical system 10 is provided with an exciter filter and an imaging optical system 30 is provided with a barrier filter in the same way as conventional retinal cameras.

The retinal camera unit 2 is provided with a chin rest and a forehead placement for supporting the face of the subject. Moreover, the retinal camera unit 2 is provided with the illumination optical system 10 and the imaging optical system 30. The illumination optical system 10 irradiates illumination light to the fundus Ef. The imaging optical system 30 guides a fundus reflected light of the illumination light to imaging devices (CCD image sensors 35, 38 (sometimes referred to simply as CCD)). Moreover, the imaging optical system 30 guides signal light input from the OCT unit 100 to the fundus Ef, and guides the signal light returned from the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near-infrared after passing through a visible cut filter 14 via a condenser lens 13. Furthermore, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding region of an aperture part) of an aperture mirror 21, transmitted through a dichroic mirror 46, and refracted by an object lens 22, thereby illuminating the fundus Ef. It should be noted that LED (Light Emitting Diode) may be used as the observation light source.

The fundus reflection light of the observation illumination light is refracted by the object lens 22, transmitted through the dichroic mirror 46, passes through the aperture part formed in the center region of the aperture mirror 21, transmitted through a dichroic mirror 55, travels through a focusing lens 31, and reflected by a mirror 32. Furthermore, the fundus reflection light is transmitted through a half-mirror 39A, refracted by reflected by a dichroic mirror 33, and forms an image on the light receiving surface of the CCD image sensor 35 by a condenser lens 34. The CCD image sensor 35 detects the fundus reflection light at a preset frame rate, for example. An image (observation image) based on the fundus reflection light detected by the CCD image sensor 35 is displayed on a display device 3. It should be noted that when the imaging optical system is focused on the anterior eye part, the observation image of the anterior eye part of the eye E is displayed.

The imaging light source 15 comprises, for example, a xenon lamp. The light (imaging illumination light) output from the imaging light source 15 is irradiated to the fundus Ef via the same route as that of the observation illumination light. The fundus reflection light of the imaging illumination light is guided to the dichroic mirror 33 via the same route as that of the observation illumination light, transmitted through the dichroic mirror 33, reflected by a mirror 36, and forms an image on the light receiving surface of the CCD image sensor 38 by a condenser lens 37. An image (photographed image) based on the fundus reflection light detected by the CCD image sensor 38 is displayed on the display device 3. It should be noted that the display device 3 for displaying the observation image and the display device 3 for displaying the photographed image may be the same or different. Further, when similar photographing is carried out by illuminating the eye E with infrared light, infrared photographed image is displayed. Moreover, LED may be used as the imaging light source.

An LCD (Liquid Crystal Display) 39 displays a fixation target or a target for measuring visual acuity. The fixation target is a visual target for fixating the eye E, and is used when photographing a fundus or performing OCT measurement.

Part of the light output from the LCD 39 is reflected by the half-mirror 39A, reflected by the mirror 32, passes through the aperture part of the aperture mirror 21, refracted by the object lens 22, and projected onto the fundus Ef.

By changing a display position of the fixation target on the screen of the LCD 39, it is possible to change the fixation position of the eye E. Examples of the fixation positions of the eye E include the position for acquiring an image centered at the macula of the fundus Ef, the position for acquiring an image centered at the optic papilla, the position for acquiring an image centered at the fundus center located between the macula and the optic papilla, and so on, as in conventional retinal cameras. Further, the display position of the fixation target may be arbitrarily changed.

Furthermore, as with conventional retinal cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from an LED 51 of the alignment optical system 50 passes through diaphragms 52 and 53 and a relay lens 54, is reflected by the dichroic mirror 55, passes through the aperture part of the aperture mirror 21, is transmitted through the dichroic mirror 46, and is projected onto the cornea of the eye E by the object lens 22.

Cornea reflection light of the alignment light passes through the object lens 22, the dichroic mirror 46 and the aperture part, a part of the cornea reflection light is transmitted through the dichroic mirror 55, passes through the focusing lens 31, reflected by the mirror 32, transmitted through the half-mirror 39A, reflected by the dichroic mirror 33, and projected onto the light receiving surface of the CCD image sensor 35 by the condenser lens 34. An image (alignment target) captured by the CCD image sensor 35 is displayed on the display device 3 together with the observation image. The user conducts alignment by an operation that is the same as conventional retinal cameras. Further, alignment may be performed in a way in which the arithmetic and control unit 200 analyzes the position of the alignment target and controls the movement of the optical system (automatic alignment function).

In order to conduct focus adjustment, the reflection surface of a reflection rod 67 is positioned at a slanted position on the optical path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light passes through the relay lens 20, is reflected at the aperture mirror 21, is transmitted through the dichroic mirror 46, is refracted by the object lens 22, and is projected onto the fundus Ef.

The fundus reflection light of the focus light passes through the same route as the cornea reflection light of the alignment light and is detected by the CCD image sensor 35. An image (split target) captured by the CCD image sensor 35 is displayed on the display device 3 together with the observation image. The arithmetic and control unit 200, as in the conventional technology, analyzes the position of the split target, and moves the focusing lens 31 and the focus optical system 60 for focusing (automatic focusing function). Further, focusing may be performed manually while visually recognizing the split target.

The dichroic mirror 46 splits the optical path for OCT from the optical for eye fundus photographing. The dichroic mirror 46 reflects light of the wavelength band used for OCT, and transmits the light for eye fundus photographing. The optical path for OCT is provided with a collimator lens unit 40, an optical path length changing part 41, a galvano scanner 42, a focusing lens 43, a mirror 44 and a relay lens 45.

The optical path length changing part 41 is capable of moving in the direction indicated by the arrow in FIG. 1 to change the length of the optical path for OCT. This change of optical path length may be used for correction of the optical path length in accordance with the axial length of the eye E, and for adjustment of the condition of interference. The optical path length changing part 41 is configured to comprise a corner cube and a mechanism for moving the corner cube, for example.

The galvano scanner 42 changes the travelling direction of light (signal light LS) travelling along the optical path for OCT. Thereby, the fundus Ef is scanned by the signal light LS. The galvano scanner 42 is configured to comprise a galvano mirror for scanning with the signal light LS in the x-direction, a galvano mirror for scanning in the y-direction, and a mechanism for independently driving these. Thereby, the signal light LS may be scanned in an arbitrary direction in the xy-plane.

[OCT Unit]

An example of the configuration of the OCT unit 100 is explained while referring to FIG. 2. The OCT unit 100 is provided with an optical system for obtaining an OCT image of the fundus Ef. The optical system comprises a similar configuration to a conventional Spectral Domain OCT apparatus. That is to say, this optical system is configured to split low-coherence light into signal light and reference light, superpose the signal light returned form the fundus Ef and the reference light having traveled through a reference optical path to generate interference light, and detect the spectral components of the interference light. This detection result (detection signal) is transmitted to the arithmetic and control unit 200.

It should be noted that when Swept Source OCT apparatus is used, a swept source is provided instead of a low-coherence light source while an optical member for spectrally decomposing interference light is not provided. In general, any known technology in accordance with the type of OCT may be arbitrarily applied for the configuration of the OCT unit 100.

A light source unit 101 outputs broadband low-coherence light L0. The low-coherence light L0, for example, includes near-infrared wavelength band (about 800-900 nm) and has a coherence length of about tens of micrometer. Moreover, it is possible to use, as the low-coherence light L0, near-infrared light having wavelength band that is impossible to be detected by human eyes, for example, infrared light having the center wavelength of about 1050-1060 nm.

The light source unit 101 is configured to comprise light output device, such as an SLD (super luminescent diode), LED, SOA (Semiconductor Optical Amplifier) and the like.

The low-coherence light L0 output from the light source unit 101 is guided to a fiber coupler 103 by an optical fiber 102 and split into the signal light LS and the reference light LR.

The reference light LR is guided to an optical attenuator 105 by an optical fiber 104. Through any known technology, the optical attenuator 105 received control of the arithmetic and control unit 200 for automatically adjusting light amount (light intensity) of the reference light LR guided to the optical fiber 104. The reference light LR having adjusted by the optical attenuator 105 is guided to a polarization controller 106 by the optical fiber 104. The polarization controller 106 is a device configured to, for example, apply stress to the loop-form optical fiber 104 from outside to adjust polarization condition of the reference light LR being guided in the optical fiber 104. It should be noted that the configuration of the polarization controller 106 is not limited to this, and arbitrary known technology may be applied. The reference light LR having adjusted by the polarization controller 106 is guided to an optical coupler 109.

The signal light LS generated by the fiber coupler 103 is guided by the optical fiber 107, and converted into a parallel light flux by the collimator lens unit 40. Further, the signal light LS travels through the optical path length changing part 41, the galvano scanner 42, the focusing lens 43, the mirror 44 and the relay lens 45, and reaches the dichroic mirror 46. Further, the signal light LS is reflected by the dichroic mirror 46, refracted by the objective lens 22, and projected to the fundus Ef. The signal light LS is scattered (including reflection) at various depth positions of the fundus Ef. The back-scattered light of the signal light LS from the fundus Ef travels along the same route as the outward way in the opposite direction to the fiber coupler 103, and is reached the fiber coupler 109 through an optical fiber 108.

The fiber coupler 109 superposes the back-scattered light of the signal light LS and the reference light LR having passed through the optical coupler 103. Interference light LC thus generated is guided by an optical fiber 110 and output from an exit end 111. Furthermore, the interference light LC is converted into a parallel light flux by a collimator lens 112, spectrally divided (spectrally decomposed) by a diffraction grating 113, converged by a condenser lens 114, and projected onto the light receiving surface of a CCD image sensor 115. It should be noted that although the diffraction grating 113 shown in FIG. 2 is of transmission type, any other kind of a spectrally decomposing element (such as reflection type) may be used.

The CCD image sensor 115 is for example a line sensor, and detects the respective spectral components of the spectrally decomposed interference light LC and converts the components into electric charges. The CCD image sensor 115 accumulates these electric charges, generates a detection signal, and transmits the detection signal to the arithmetic and control unit 200.

Although a Michelson-type interferometer is employed in this embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, may be used.

[Arithmetic and Control Unit]

A configuration of the arithmetic and control unit 200 will be described. The arithmetic and control unit 200 analyzes the detection signals input from the CCD image sensor 115 to form an OCT image of the fundus Ef. Arithmetic processing for this may be the same as that of a conventional Spectral Domain OCT apparatus.

Further, the arithmetic and control unit 200 controls each part of the retinal camera unit 2, the display device 3 and the OCT unit 100. For example, the arithmetic and control unit 200 causes the display device 3 to display an OCT image of the fundus Ef.

Further, as controls of the retinal camera unit 2, the arithmetic and control unit 200 executes: controls of actions of the observation light source 101, the imaging light source 103 and LED's 51 and 61; control of action of the LCD 39; controls of movements of the focusing lenses 31 and 43; control of movement of the reflection rod 67; control of movement of the focus optical system 60; control of movement of the optical path length changing part 41; control of action of the galvano scanner 42; and so on.

Further, as controls of the OCT unit 100, the arithmetic and control unit 200 executes: control of action of the light source unit 101; control of action of the optical attenuator 105; control of action of the polarization controller 106; control of action of the CCD image sensor 115; and so on.

The arithmetic and control unit 200 comprises a microprocessor, a RAM, a ROM, a hard disk drive, a communication interface, and so on, as in conventional computers. The storage device such as the hard disk drive stores a computer program for controlling the fundus observation apparatus 1. The arithmetic and control unit 200 may be provided with various circuit boards such as a circuit board for forming OCT images. Moreover, the arithmetic and control unit 200 may be provided with operation devices (input devices) and/or a display device. The operation devices include a pointing device such as a mouse, and a keyboard, for example. The display device is a flat panel display such as an LCD, for example.

The retinal camera unit 2, the display device 3, the OCT unit 100, and the arithmetic and control unit 200 may be integrally configured (that is, provided within a single case), or separately configured in two or more cases.

[Control System]

Figure 3:
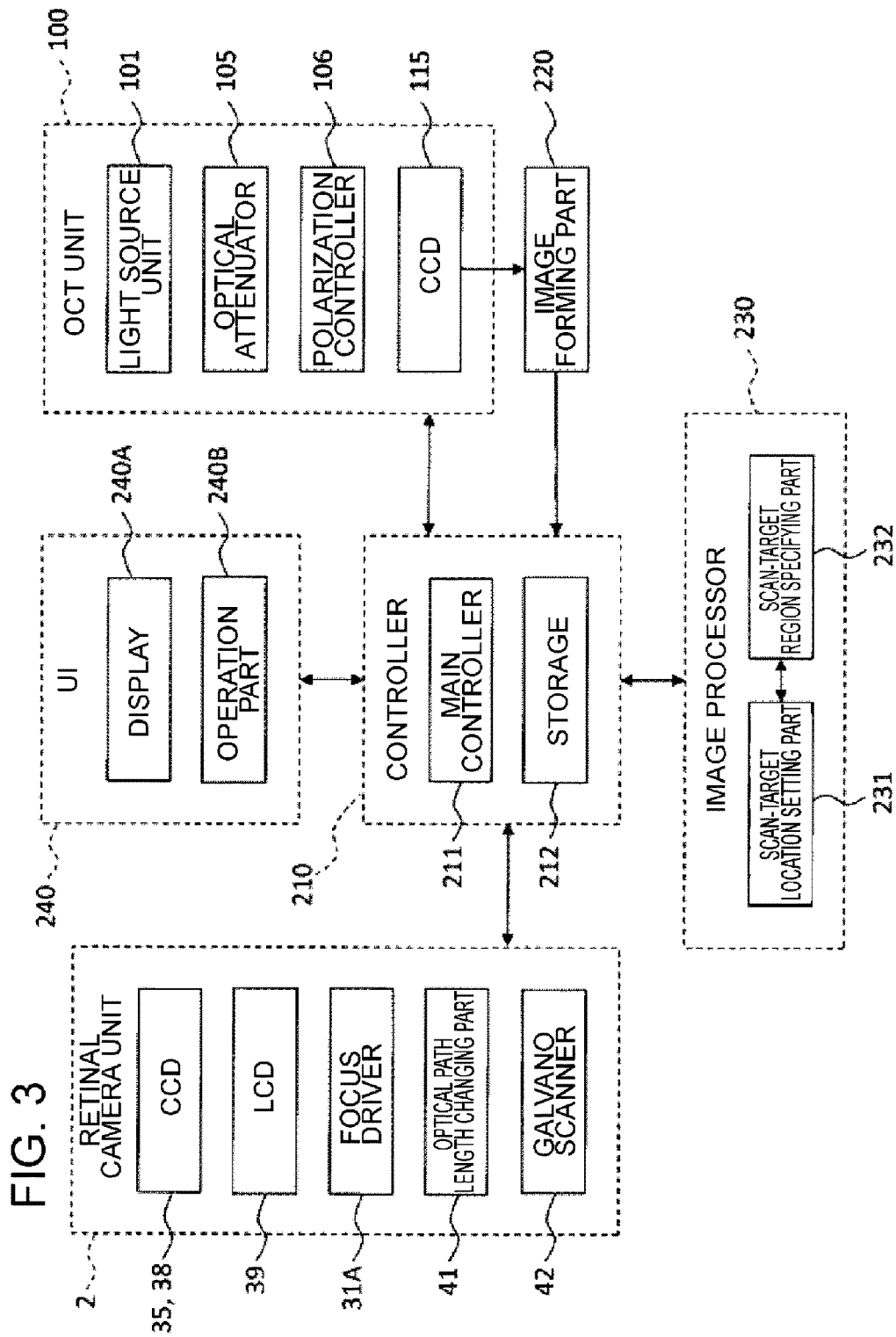
FIG. 3 is a schematic block diagram showing an example of a configuration of a fundus observation apparatus according to an embodiment.
Figure 4:
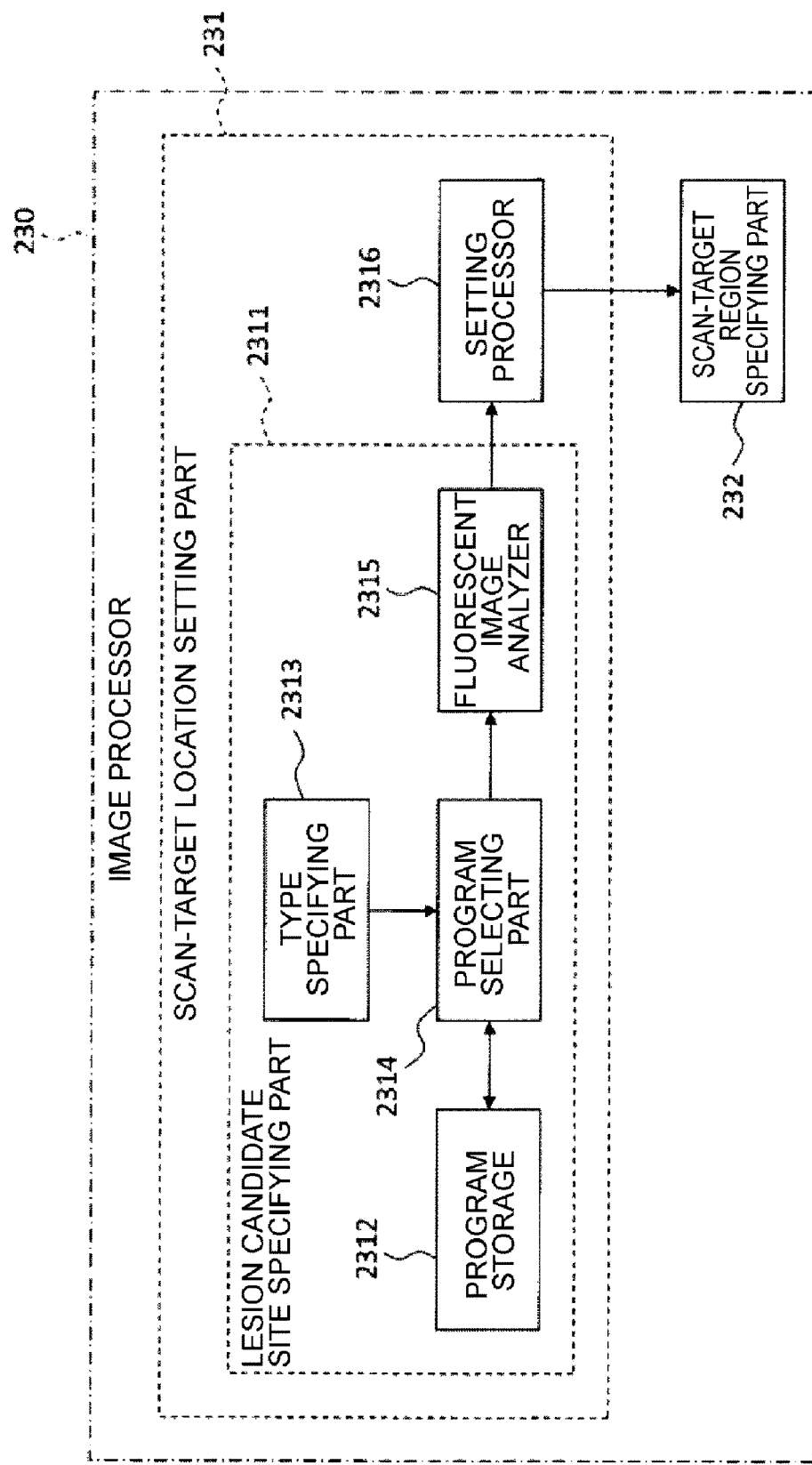
FIG. 4 is a schematic block diagram showing an example of a configuration of a fundus observation apparatus according to an embodiment.

A configuration of a control system of the fundus observation apparatus 1 will be described with reference to FIGS. 3 and 4.

(Controller)

The control system of the fundus observation apparatus has a configuration centered on a controller 210 The controller 210 is configured to comprise, for example, the aforementioned microprocessor, RAM, ROM, hard disk drive, and communication interface, etc. The controller 210 is provided with a main controller 211 and storage 212.

(Main Controller)

The main controller 211 performs the aforementioned various kinds of controls. Specifically, the main controller 211 controls a focus driver 31A, the optical path length changing part 41 and the galvano scanner 42 of the retinal camera unit 2, and further controls the light source unit 101, the optical attenuator 105 and the polarization controller 106 of the OCT unit 100. The main controller 211 functions as an example of "controller".

The focus driver 31A moves the focusing lens 31 in the direction of the optical axis. Thereby, the focus position of the imaging optical system 30 is changed. It should be noted that the main controller 211 may control an optical system driver (not shown in diagrams) to three dimensionally move the optical system provided in the retinal camera unit 2. This control is used for alignment and tracking. Tracking is an operation for move the optical system in accordance with eye movement of the eye E. When tracking is applied, alignment and focusing are carried out in advance. Tracking is a function to maintain adequate positional relationship in which alignment and focusing are matched by causing the position of the optical system to follow the eye movement.

The main controller 211 executes a process of writing data into the storage 212, and a process of reading out data from the storage 212.

(Storage)

The storage 212 stores various kinds of data. The data stored in the storage 212 may include image data of OCT images, image data of fundus images, and eye information, for example. The eye information includes information on the eye, such as information on a subject such as a patient ID and a name, identification information on left eye or right eye, and so on. Further, the storage 212 stores various programs and data for operating the fundus observation apparatus 1. It should be noted that although analysis programs for analyzing fluorescent images are stored in a program storage 2312 (explained later) in this embodiment, such analysis programs may be stored in the storage 212.

(Image Forming Part)

An image forming part 220 forms image data of a tomographic image of the fundus Ef based on the detection signals from the CCD image sensor 115. Like conventional Spectral Domain OCT, this process includes processes such as noise elimination (noise reduction), filtering and FFT (Fast Fourier Transform). In the case in which other OCT type is applied, the image forming part 220 executes known process in accordance with the applied OCT type. The image forming part 220 serves as an example of "tomographic image forming part" together with the optical system for OCT (including the interference optical system and the galvano scanner 42). Further, the galvano scanner 42 functions as an example of "scanner".

The image forming part 220 comprises the aforementioned circuit board, for example. It should be noted "image data" and the "image" based on the image data may be identified with each other in the description.

(Image Processor)

An image processor 230 executes various image processing and analysis processing on images formed by the image forming part 220. For example, the image processor 230 executes various correction processing such as brightness correction, dispersion correction of images, etc. Further, the image processor 230 executes various image processing and analysis processing on images obtained by the retinal camera unit 2 (fundus images, anterior eye part images, etc.).

The image processor 230 executes known image processing such as interpolation processing for interpolating pixels between tomographic images to form image data of a three-dimensional image of the fundus Ef. It should be noted that the image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as a display 240A, this pseudo three-dimensional image is displayed.

Further, it is also possible to form stack data of multiple tomographic images as the image data of a three-dimensional image. Stack data is image data obtained by three-dimensionally arranging multiple tomographic images obtained along multiple scanning lines, based on the positional relation of the scanning lines. That is to say, stack data is image data obtained by expressing multiple tomographic images defined by originally individual two-dimensional coordinate systems by a three-dimensional coordinate system (in other words, embedding into a three-dimensional space).

The image processor 230 is provided with a scan-target location setting part 231 and a scan-target region specifying part 232.

(Scan-Target Location Setting Part)

The scan-target location setting part 231 processes a fluorescent image. More specifically, the scan-target location setting part 231 sets a scan-target location of the signal light LS on a fluorescent image displayed on the display 240A. The fluorescent image is an example of "distribution information". Further, the scan-target location setting part 231 is an example of "setting part".

This fluorescent image may be an image captured by applying a fluorescent agent to a subject such as a fluorescein contrast image, indocyanine green contrast image, etc. or may be an autofluorescent image without a fluorescent agent. The scan-target location refers to a location to which OCT measurement is to be applied, in other words, a location in which scanning by the signal light LS is to be applied.

The scan-target location may be arbitrarily set. For example, the user can set a desired scan-target location by manipulating an operation part 240B. Alternatively, a scan-target location can be automatically set such that it passes through a certain region in the fluorescent image. This certain region may be a characteristic site of a fundus such as an optic disc, macula, blood vessel, etc., or may be a site of a fundus that is considered to be a lesion (referred to as a lesion candidate site). Here, the case is explained in which a lesion candidate site in a fluorescent image is automatically set).

The scan-target location setting part 231 comprises a lesion candidate site specifying part 2311 and a setting processor 2316.

(Lesion Candidate Site Specifying Part)

The lesion candidate site specifying part 2311 analyzes a fluorescent image to specify a lesion candidate site of the fundus Ef. The lesion candidate site specifying part 2311 functions as an example of "analyzer". The processing for specifying a lesion candidate site is arbitrary. For example, the lesion candidate site specifying part 2311 executes this processing by a program storage 2312, a type specifying part 2313, a program selecting part 2314 and a fluorescent image analyzer 2315.

(Program Storage)

The program storage 2312 previously stores an analysis program for analyzing a fluorescent image. In this embodiment, two or more analysis programs corresponding to two or more types of fluorescent images are stored in the program storage 2312. The program storage 2312 is an example of "first storage".

As mentioned before, the types of fluorescent images include ones captured with a fluorescent agent and ones captured without a fluorescent agent. Fluorescent images captured with a fluorescent agent include ones captured by applying various fluorescent agents such as fluorescein and indocyanine green, etc. The analysis program is provided for each of such types. It should be noted that it is possible to provide analysis programs by putting some types together and regarding these as a single type. In this embodiment, a first type that is captured by applying a fluorescent agent and a second type that is captured without a fluorescent agent are considered. Therefore, a first analysis program corresponding to the first type and a second analysis program corresponding to the second type are stored in the program storage 2312 in advance. The association between the types of fluorescent images and the analysis programs is previously stored, for example, as table information in the program storage 2312. It should be noted that image analysis processing based on these analysis programs are explained later.

The first program is configured for specifying a lesion candidate site from among image regions with high brightness in a fluorescent image of the first type (that is, a fluorescent image captured with a fluorescent agent). Acquisition of a fluorescent image of the first type is carried out by detecting fluorescence emitted from a fluorescent agent that receives excitation light obtained by using an exciter filter. Therefore, sites emitting fluorescence such as an optic disc, blood vessel, dye leaking site are depicted relatively brightly while other sites are depicted relatively darkly. The first analysis program is configured by considering such brightness characteristics.

The second program is configured for specifying a lesion candidate site from among image regions with high brightness in a fluorescent image of the second type (that is, a fluorescent image captured without a fluorescent agent). Acquisition of a fluorescent image of the second type is carried out by detecting fluorescence emitted from lipofuscin in retinal pigment epithelium (RPE). Therefore, sites in which RPE does not exist (and sites in which almost no RPE exists) such as an optic disc and blood vessel are depicted relatively darkly while other sites (for example, dye leaking sites) are depicted relatively brightly. The second analysis program is configured by considering such brightness characteristics.

(Type Specifying Part)

The type specifying part 2313 specifies the type of the fluorescent image that is a processing object. The type specifying part 2313 functions as an example of "first type specifying part". Here, two processing examples of specifying the type are explained; however, the processing is not limited to these methods, and arbitrary method may be applied.

The first example of the processing of specifying the type of a fluorescent image is carried out based on brightness of a characteristic site of the fundus Ef in the fluorescent image. This characteristic site may be an optic disc and/or blood vessels, for example. The following is the explanation of this processing example.

Firstly, the type specifying part 2313 specifies an image region (pixels) corresponding to a characteristic site based on distribution of pixel values (brightness) of a fluorescent image. This processing is carried out by using threshold processing related to brightness and/or shape analysis of image regions (such as pattern matching), for example. When an image region corresponding to an optic disc, an image region is searched in which brightness is higher (or lower) than its vicinity and the shape is substantially circular or substantially elliptic. When an image region corresponding to a blood vessel, an image region is searched in which brightness is higher (or lower) than its vicinity and the shape is substantially linear.

Next, the type specifying part 2313 specifies the type of the fluorescent image based on the brightness of the specified image region and the brightness of its vicinity. An concrete example of this processing is explained. When the brightness of the specified image region (for example, the image region corresponding to a blood vessel) is higher than its vicinity (for example, the image region corresponding to a site other than a blood vessel), the type specifying part 2313 judges that the target fluorescent image is of the first type that is captured with a fluorescent agent. On the other hand, when the brightness of the specified image region is lower than its vicinity, the type specifying part 2313 judges that the target fluorescent image is of the second type that is captured without a fluorescent agent. It should be noted that comparison processing of brightness is carried out, for example, by calculating the mean value of the brightness values of the pixels included in the both image regions. In this case, the calculation of the mean value may be carried out by extracting an image region of preset size as an image region of vicinity.

The second example of processing of specifying the type of fluorescent images is explained. In this example, identification information indicating the type is associated with a fluorescent image in advance. Examples of this identification information include supplementary information (DICOM tag) of the DICOM (Digital Imaging and COmmunications in Medicine) that is a standard specification of medical images. This supplementary information is given to a fluorescent image at the time of or after fluorescence imaging. Other examples of identification information may be electronic medical record information. In an electronic medical record, a dedicated or general-purpose input space is provided for inputting the type of a fluorescent image. At the time of or after fluorescence imaging, identification information is input into this input space manually or automatically. The automatic input is carried out, for example, based on a signal input from a fundus imaging apparatus used for fluorescence imaging. When the type of fluorescence imaging is determined in advance (such as when clinical path is applied), automatic input is carried out based on this predetermined information.

The type specifying part 2313 specifies the type of the target fluorescent image based on identification information such as the above.

(Program Selecting Part)

The program selecting part 2314 selects an analysis program corresponding to the type specified by the type specifying part 2313 from among the analysis programs stored in the program storage 2312. This processing is carried out, for example, by referring to the abovementioned table information previously stored in the program storage 2312. The program selecting part 2314 functions as an example of "first selecting part".

(Fluorescent Image Analyzer)

The fluorescent image analyzer 2315 analyzes the fluorescent image using the analysis program selected by the program selecting part 2314 to specify a lesion candidate site. An example of this processing is explained for each of the first type and the second type.

The case in which a fluorescent image of the first type with fluorescent agent is analyzed, that is, the case in which a fluorescent image is analyzed using a first analyze program is explained. In a fluorescent image of the first type, the brightness of blood vessels and dye leaking sites is high. It should be noted that the result of the abovementioned image processing by the type specifying part 2313 may be used in the following processing.

First, the fluorescent image analyzer 2315 specifies an image region in the target fluorescent image in which brightness is high.

Next, the fluorescent image analyzer 2315 specifies a lesion candidate site from among the high-brightness image region specified. This processing is carried out, for example, by dividing the high-brightness image region into connected regions and determining whether or not each connected region is a lesion candidate site based on the shape of the connected region. Here, a connected region means a set of adjacent pixels according to the mathematical term "connectedness". The fluorescent image analyzer 2315 classifies the pixels included in the high-brightness image region into sets consisting of adjacent pixels (that is, into connected regions). Further, the fluorescent image analyzer 2315 determines whether or not the shape of each of the connected regions is linear. Then, the fluorescent image analyzer 2315 defines the connected region determined to be linear as an image region corresponding to a blood vessel, and defines other connected regions as dye leaking sites. The image regions defined as dye leaking sites are regarded to be lesion candidate sites. It should be noted that connected regions of the size smaller than a preset size (that is, connected regions including fewer pixels than a preset number) can be ignored because they may be noises.

The case in which a fluorescent image of the second type without fluorescent agent is analyzed, that is, the case in which a fluorescent image is analyzed using a second analyze program is explained. In a fluorescent image of the second type, the brightness of an optic disc and blood vessels is low, and the brightness of dye leaking sites high. As a processing example of this case, the fluorescent image analyzer 2315 firstly specifies image regions with especially low brightness in a fluorescent image. Such image regions correspond to an optic disc and blood vessels. Next, the fluorescent image analyzer 2315 specifies image regions with relatively high brightness in image regions other than the image regions with especially low brightness. Such image regions with relatively high brightness correspond to dye leaking sites (lesion candidate sites).

It should be noted that although specification processing of each image region by the second analysis program is similar to that by the first analysis program, algorithm (flow of processing) for specifying dye leaking sites is different as explained above.

(Setting Processor)

The setting processor 2316 sets a scan-target location on the fluorescent image based on the lesion candidate site specified by the lesion candidate site specifying part 2311. An example of this setting processing is explained. This example of processing comprises processing of selecting the pattern of a scan-target location and processing of determining the location in the fluorescent image on which the scan-target location is set.

First, the setting processor 2316 carries out processing of selecting the pattern of a scan-target location. The pattern may be patterns corresponding to scanning patterns of the signal light LS described later. The scanning patterns may include line scan, cruciform scan, radial scan, circular scan, concentric scan, helical scan, and so on. The selection of the pattern may be carried out manually or automatically.

In one example of the former (manual selection), the main controller 211 displays a user interface for selecting a pattern on the display 240A, and the user operates the operation part 240B to select a pattern.

In one example of the latter (automatic selection), table information associating patterns with attributes such as disease names or examination sites is stored in advance, an attribute is obtained from an electronic medical record etc., and the pattern corresponding to this attribute is selected. Alternatively, it is possible to record the pattern actually applied in an electronic medical record etc., and refer the record to apply the same pattern again.

When the pattern of the scan-target location is selected, the setting processor 2316 carry out processing of determining the location in the fluorescent image on which the scan-target location is set. This processing is carried out based on the aspect of the lesion candidate site, for example. The aspect of the lesion candidate site may be the size and/or shape.

The contents of this processing are changed according to the result of the selection of the pattern. When the pattern corresponding to line scan is selected, the setting processor 2316, for example, specifies a characteristic location (center, barycenter, site of characteristic form, etc.) of the lesion candidate site, and determines the location of a linear pattern such that it passes through this characteristic location specified. Further, when a pattern corresponding to a scanning pattern in which center position thereof exists (such as cruciform scan, radial scan, circular scan, concentric scan, helical scan) is selected, the setting processor 2316, for example, specifies a characteristic location of the lesion candidate site, and determines the location of the pattern such that the center position of the pattern is located at this characteristic location specified. Further, when three-dimensional scan is selected, it is possible to determine the location of the rectangular pattern such that the whole of the lesion candidate site is included in it.

It should be noted that when the lesion candidate site is too large (for example, when the lesion candidate site is larger than the maximum scanning field (maximum length, maximum area, etc.), the setting processor 2316 may determine the location of the pattern such that it covers only part of the lesion candidate site. Alternatively, it is possible to obtain multiple locations at which patterns are set such that they cover a region including the maximum scanning field.

(Scan-Target Region Specifying Part)

The fundus observation apparatus 1 is capable of acquiring an infrared fundus image as mentioned above. The infrared fundus image is acquired by movie-imaging the fundus Ef using infrared light. The infrared fundus image includes multiple still images (frames) acquired with a preset frame rate. Each of the frames is a monochromatic image of the fundus Ef.

The scan-target region specifying part 232 specifies the image region in the infrared fundus image corresponding to the scan-target location set by the scan-target location setting part 231. This image region is referred to as an scan-target region. The scan-target region specifying part 232 functions as an example of "specifying part". An example of processing carried out by the scan-target region specifying part 232. It should be noted that the following processing is applied to the respective frame of the infrared fundus image that is a moving image. Here, it is not necessary to apply the following processing to all of the frames of the infrared fundus image, and, for example, it may be configured to apply the processing to every preset number of frames.

The scan-target region specifying part 232 carries out matching processing between the fluorescent image and a frame of the infrared fundus image. This image matching processing is carried out, for example, by specifying image regions in the both images corresponding to a preset characteristic site of the fundus Ef, respectively, and carrying out matching processing between the specified image regions. This image matching processing establishes association between positions (coordinates) of the pixels in the fluorescent image and positions (coordinates) of the pixels in the frame. Here, the characteristic site to be specified is, for example, an optic disc, macula, blood vessel (branch point thereof), etc.

Further, the scan-target region specifying part 232 specifies the scan-target region in the frame corresponding to the scan-target location set on the fluorescent image based on the association of the pixel positions obtained by the above matching processing.

Further, the scan-target region specifying part 232 may apply similar processing to the different frames of the infrared fundus image. More specifically, the scan-target region specifying part 232 may carry out matching processing between a first frame and a second frame, and associates an image region in the first frame and an image region in the second frame with each other based on the association of pixel positions obtained by this matching processing. Such processing may be applied to processing of specifying the image region in the second frame corresponding to a scan-target region in the first frame, for example.

It is possible to configure to switch image matching processing in accordance with types of fluorescent images. In this case, similar to the lesion candidate site specifying part 2311, a program storage (second storage), a type specifying part (second type specifying part) and a program selecting part (second selecting part) are provided in the scan-target region specifying part 232.

The program storage stores two or more image analysis program corresponding to the two or more types of fluorescent images in advance. The respective image analysis programs is configured while taking into account brightness characteristics of the corresponding type of fluorescent images in a similar fashion to the abovementioned analysis programs.

The type specifying part carries out similar processing to the case of the lesion candidate site specifying part 2311 to specify the type of a concerned fluorescent image. It should be noted that the first type specifying part and the second type specifying part may be configured to be a single component. When this is the case, the result of specification processing carried out by the first type specifying part (the type specifying part 2313 in the present embodiment) is input into the second selecting part.

The program selecting part selects the image analysis program corresponding to the specified type from among the two or more image analysis programs stored in the program storage.

The scan-target region specifying part 232 uses the selected image analysis program to carry out image matching processing between the fluorescent image and (the frames of) the infrared fundus image. Then, the scan-target region specifying part 232 specifies, as a scan-target region, an image region in the infrared fundus image that is associated to the scan-target location in the fluorescent image by this image matching processing.

The image processor 230 that functions as above includes, for example, the aforementioned microprocessor, RAM, ROM, hard disk drive, circuit board, and so on. A computer program that causes the microprocessor to perform the above functions is stored in the storage device such as the hard disk drive in advance.

(User Interface)

A user interface 240 comprises the display 240A and the operation part 240B. The display 240A is configured to include a display device of the aforementioned arithmetic and control unit 200 and/or the display device 3. The operation part 240B is configured to include an operation device of the aforementioned arithmetic and control unit 200. The operation part 240B may also comprise various kinds of buttons, keys, pointing devices, etc. that are provided with the case of the fundus observation apparatus 1 or outside thereof. For example, when the retinal camera unit 2 has a case that is similar to conventional retinal cameras, a joy stick, operation panel, etc. provided with the case may also be included in the operation part 240B. Furthermore, the display 240A may also include various display devices such as a touch panel etc. provided with the case of the retinal camera unit 2.

The display 240A and the operation part 240B do not need to be configured as separate components. For example, like a touch panel, it is possible to apply a device in which the display function and the operation function are integrated. In this case, the operation part 240B is configured to include a touch panel and a computer program. A content of operation to the operation part 240B is input into the controller 210 as an electrical signal. Further, operations and/or information input may be carried out by using a graphical user interface (GUI) displayed on the display 240A and the operation part 240B.

[Scanning with Signal Light and OCT Images]

Here, scanning with the signal light LS and OCT image are described.

The scanning aspect (scanning pattern) of the signal light LS by the fundus observation apparatus 1 is, for example, a line scan, cruciform scan, radial scan, circular scan, concentric scan or helical scan, etc. These scanning aspects are selectively used as necessary taking into account an observation site of a fundus, an analysis target (retinal thickness or the like), time required for scanning, the density of scanning, and so on.

The line scan is one for scanning the signal light LS along a linear trajectory. The direction of the linear trajectory in the line scan is arbitrary. The line scan includes a horizontal scan, vertical scan and oblique scan. The horizontal scan is one for scanning the signal light LS in the horizontal direction (x-direction). The horizontal scan includes an aspect of scanning the signal light LS along multiple scanning lines extending in the horizontal direction arranged in the vertical direction (y-direction). In this aspect, it is possible to arbitrarily set the interval of scanning lines. Further, by setting the interval between adjacent scanning lines to be sufficiently narrow, it is possible to form the aforementioned three-dimensional image (three-dimensional scan). The vertical scan and the oblique are performed in a similar manner.

The cruciform scan is one for scanning the signal light LS along a cross-shape trajectory formed by two linear trajectories orthogonal to each other. Alternatively, it is possible to configure the cruciform scan by combining multiple horizontal scans and multiple vertical scans. For example, five horizontal scans and five vertical scans may be combined. The radial scan is one for scanning the signal light LS along a radial trajectory formed by multiple linear trajectories arranged at predetermined angles. It should be noted that the cruciform scan is an example of the radial scan.

The circular scan is one for scanning the signal light LS along a circular trajectory. The concentric scan is one for scanning the signal light LS along multiple circular trajectories arranged concentrically around a predetermined center position. The circular scan is an example of the concentric scan. The helical scan is one for scanning the signal light LS along a helical trajectory while making the turning radius gradually smaller (or greater).

Since the galvano scanner 42 is configured to scan the signal light LS in the directions orthogonal to each other, the galvano scanner 42 is capable of scanning the signal light LS in the x-direction and the y-direction independently. Moreover, it is possible to scan the signal light LS along an arbitrary trajectory on the xy-plane by simultaneously controlling the directions of two galvano mirrors included in the galvano mirror 42. Thus, various types of scanning aspects as described above may be realized.

By scanning the signal light LS in the aspect described above, it is possible to obtain a tomographic image in the plane spanned by the direction along the scanning line and the depth direction (z-direction) of the fundus. Moreover, in a case in which the interval between scanning lines is narrow, it is possible to obtain the aforementioned three-dimensional image.

A region on the fundus Ef subjected to scanning by the signal light LS as above, that is, a region on the fundus Ef subjected to OCT measurement, is referred to as a scanning region. This scanning region is substantially realized by scanning the signal light LS based on the scan-target location set on a fluorescent image. A scanning region for the three-dimensional scan is a rectangular-shaped region in which multiple horizontal scans are arranged. Furthermore, a scanning region for the concentric circular scan is a disc-shaped region surrounded by the trajectories of a circular scan of a maximum diameter. Moreover, the scanning region for the radial scan is a disc-shaped (or polygonal-shaped) region linking end positions of the scanning lines.

[Operation]

Figure 5:
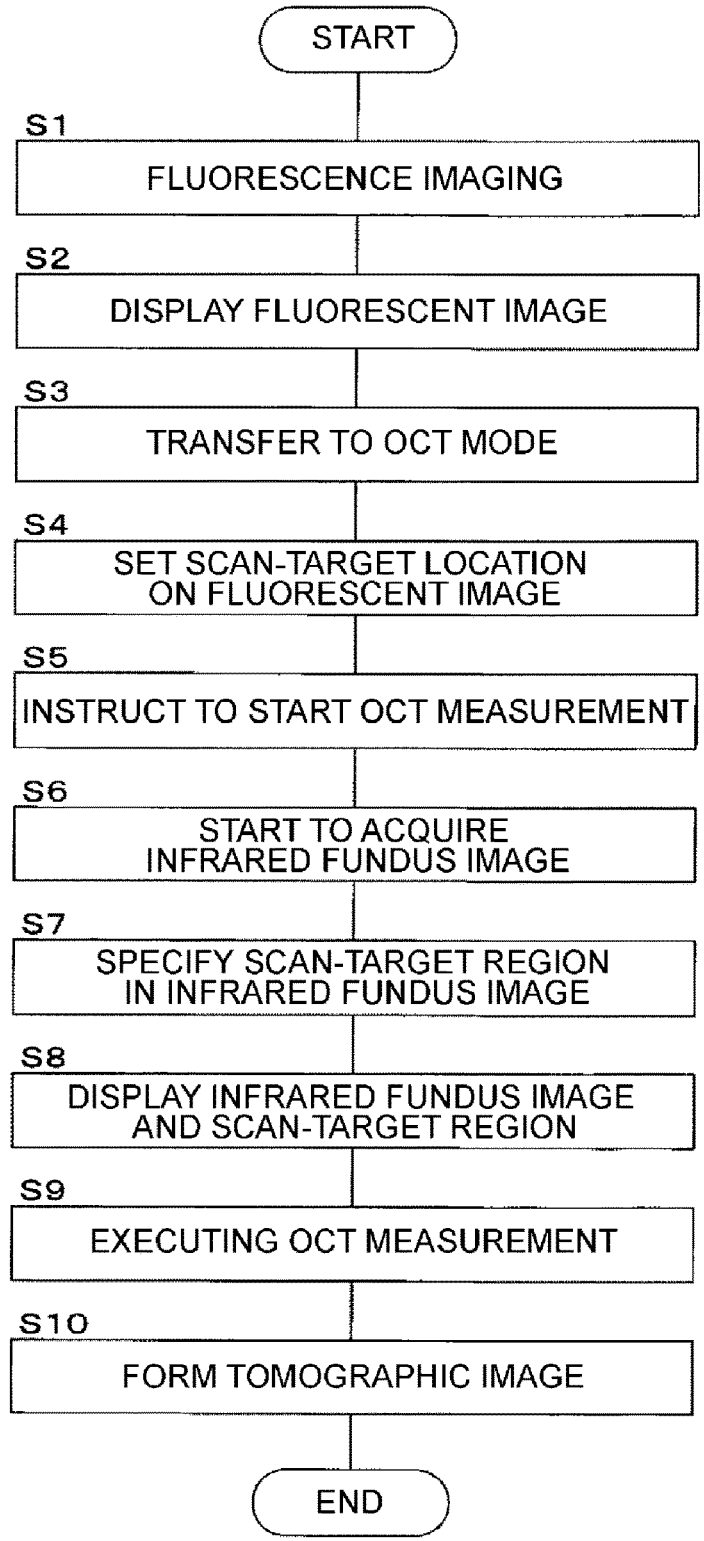
FIG. 5 is a flowchart showing an example of an operation of a fundus observation apparatus according to an embodiment.

The operation of the fundus observation apparatus 1 will be described. FIG. 5 illustrates an example of the operation of the fundus observation apparatus 1. It is assumed that preparation for fundus imaging (alignment, focusing, fixation of the eye, etc.) has already done.

In the following example of operation, the case is explained in which fluorescence imaging and OCT measurement are successively carried out. Alternatively, it is possible to configure to store an infrared image obtained by the fundus observation apparatus 1 in the fundus observation apparatus 1 or other apparatus and read out the infrared image to use it, or it is possible to configure to store an infrared image obtained by another apparatus in the fundus observation apparatus 1 or other apparatus and read out the infrared image to use it. The "other apparatus" may be PACS (Picture Archiving and Communication Systems), ophthalmological image database, fundus imaging apparatus that has carried out fluorescence imaging, etc.

(S1: Fluorescence Imaging)

Fluorescence imaging of the fundus Ef is carried out. For the fluorescence imaging, an exciter filter and a barrier filter are located in the optical path, and imaging illumination light emitted from the imaging light source 15 is used.

(S2: Display Fluorescent Image)

Figure 6:
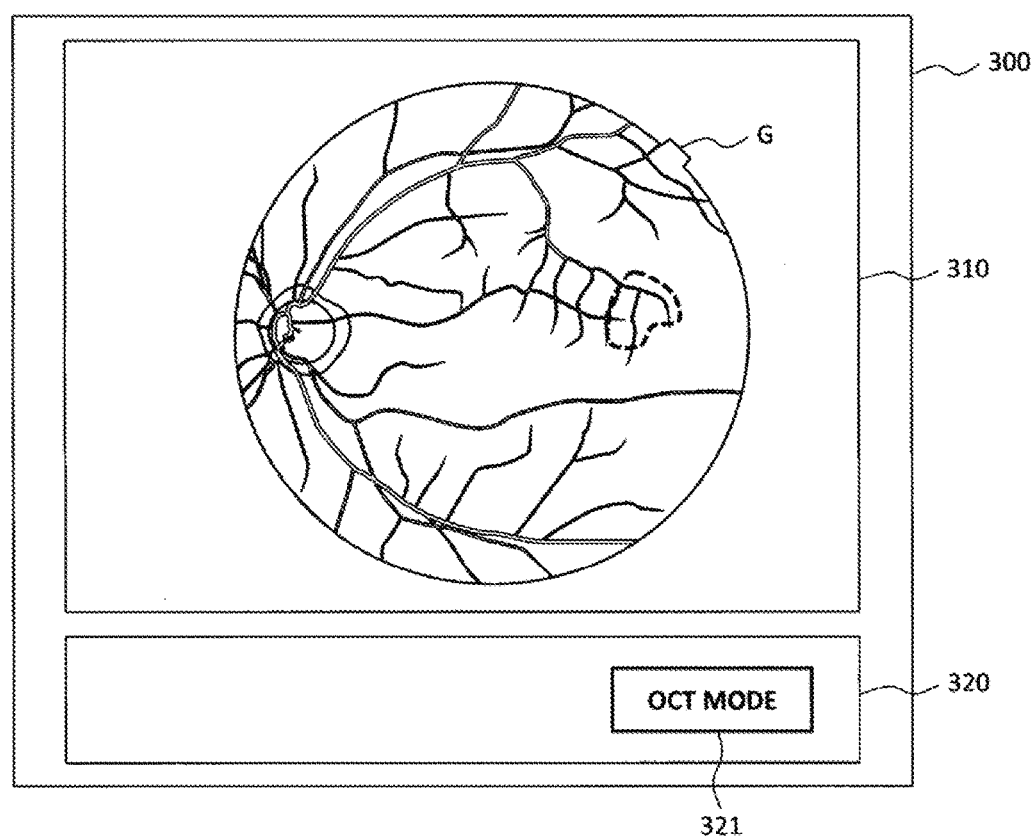
FIG. 6 is a schematic diagram for explaining an operation of a fundus observation apparatus according to an embodiment.

The main controller 211 displays the fluorescent image obtained in Step 1 on the display 240A. An example of a display screen is illustrated in FIG. 6. In a display screen 300, an image display part 310 and GUI part 320 are provided. A fluorescent image G is displayed in the image display part 310 by the main controller 211. Various kinds of GUIs are displayed in the GUI part 320. At this stage, an OCT mode button 321 is provided in the GUI part 320. The OCT mode button 321 is operated for transferring to an operation mode (OCT mode) for executing OCT measurement.

(S3: Transfer to OCT Mode)

Figure 7:
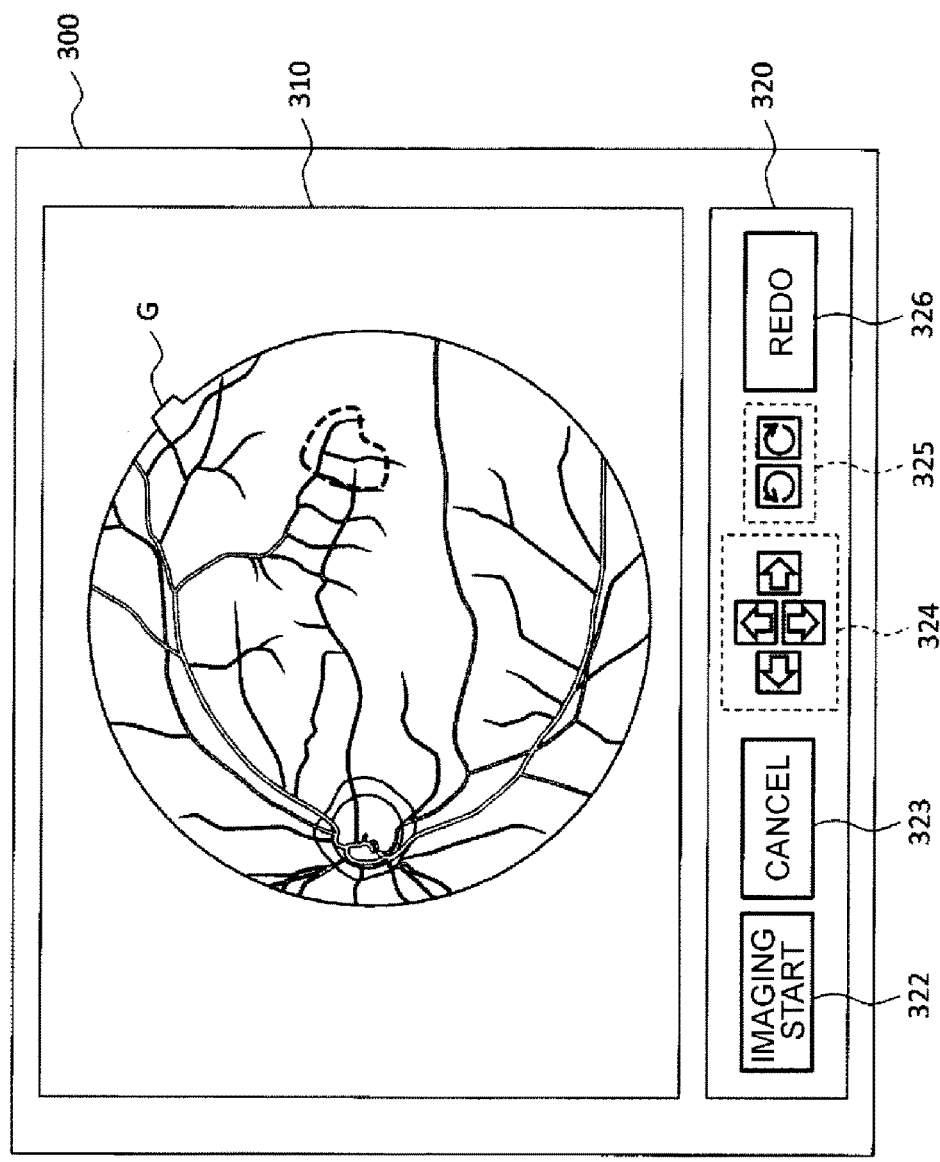
FIG. 7 is a schematic diagram for explaining an operation of a fundus observation apparatus according to an embodiment.

When the user manipulates a mouse (operation part 240B) to click the OCT mode button 321, the main controller 211 changes the contents displayed in the GUI part 320 of the display screen 300. Thereby, the display screen becomes the aspect illustrated in FIG. 7.

In the GUI part 320, an imaging start button 322, cancel button 323, translation button 324, rotation button 325, and redo button 326 are displayed. The imaging start button 322 is clicked for starting OCT measurement. The cancel button 323 is clicked for removing from the OCT mode.

The translation button 324 is clicked for translating (performing parallel displacement) the set scan-target location. In this operation example, as the translation button 324, buttons for translating the scan-target location upward, downward, leftward and rightward, respectively, are provided. When the translation button 324 is clicked once, the main controller 211 moves the scan-target location by preset distance. The translation button 324 is an example of a "first operation part".

The rotation button 325 is clicked for rotating the set scan-target location. In this operation example, as the rotation button 325, a buttons for clockwise rotation and a buttons for counterclockwise rotation are provided. When the rotation button 325 is clicked once, the main controller 211 rotates the scan-target location by preset angle. The rotation button 325 is an example of a "second operation part".

The redo button 326 is operated after performing translation and/or rotation of the scan-target location, and is clicked for returning the scan-target location to the state before the translation and/or rotation. It should be noted that modes of control in accordance with clicking the redo button 326 may include control of returning the scan-target location to the initial state, control of returning the scan-target location to the state immediately before the last moving operation, etc.

(S4: Set Scan-Target Location on Fluorescent Image)

Next, setting of a scan-target location is carried out automatically or manually.

In the case of automatic setting, as described above, the type specifying part 2313 specifies the type of the fluorescent image, the program selecting part 2314 selects the analysis program corresponding to the specified type, and the fluorescent image analyzer 2315 specifies a lesion candidate site based on the selected analysis program. Then, the setting processor 2316 sets a scan-target location based on the specified lesion candidate site. The main controller 211 displays information indicating the set scan-target location over the fluorescent image G. This information displayed is, for example, image information displayed over the scan-target location. When the scan-target location is two-dimensional, image information indicating the contour of the scan-target location may be displayed. Alternatively, it is possible to display image information indicating the scan-target location, such as image information indicating both ends of a linear pattern, in the surrounding region of the scan-target location.

In the case of manual setting, the user, for example, manipulate the operating part 240B (pointing device such as a mouse) to input a desired scan-target location on the displayed fluorescent image. The main controller 211 displays information indicating the input scan-target location. This information displayed may be similar to that in the automatic case.

Figure 8:
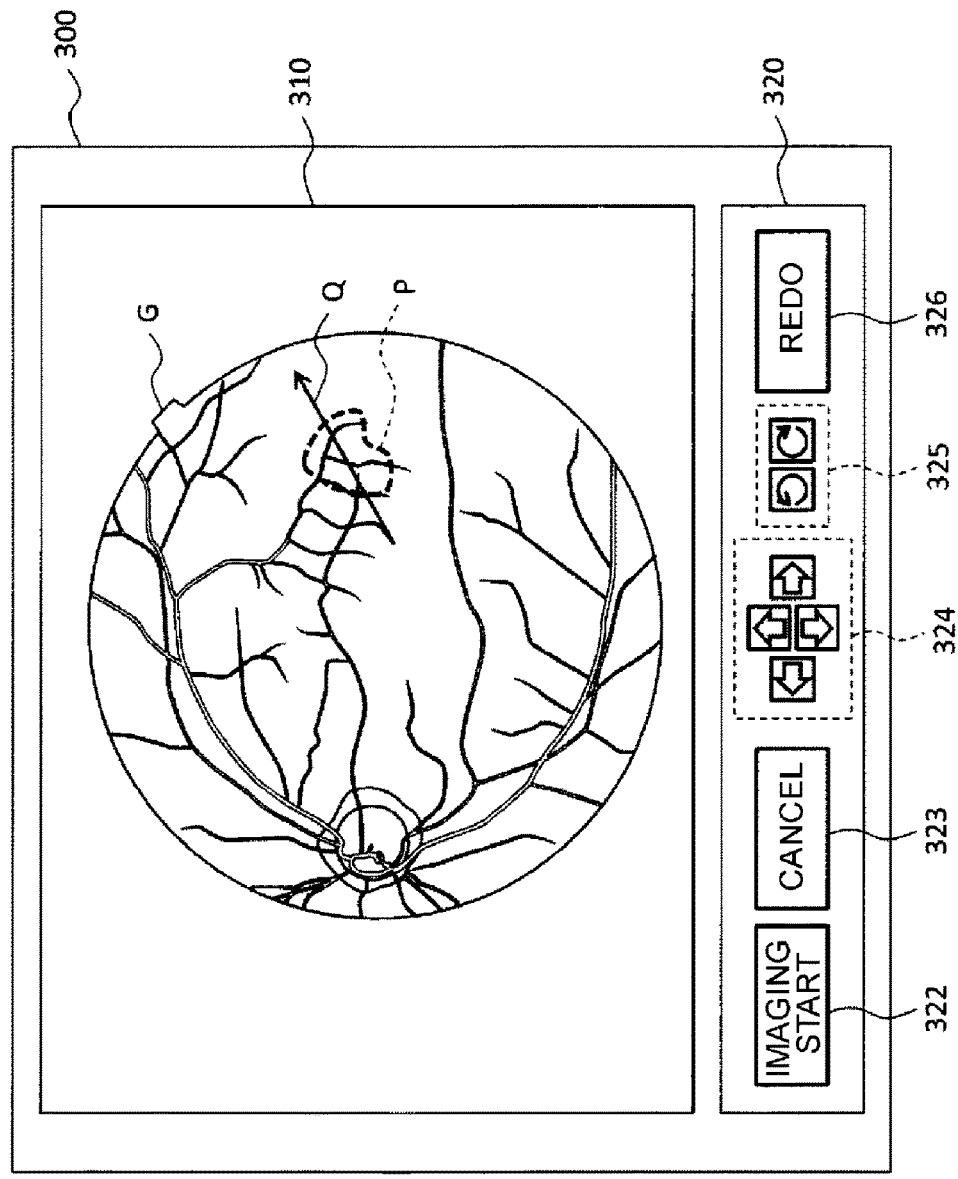
FIG. 8 is a schematic diagram for explaining an operation of a fundus observation apparatus according to an embodiment.

FIG. 8 illustrates an example of an aspect of displaying the scan-target location set. The symbol "P" indicates a lesion candidate site. Further, the arrow indicated by the symbol "Q" is displayed information indicating the scan-target location for a linear pattern. This arrow indicates the direction for scanning the signal light LS.

The user may use the translation button 324 and the rotation button 325 to change the scan-target location provisionally set.

(S5: Instruct to Start OCT Measurement)

When the setting of the scan-target location is completed, the user instructs the apparatus to start OCT measurement by clicking the imaging start button 322 by using the operation part 240B. Upon receiving this instruction, the main controller 211 starts preparation operations of OCT measurement as follows.

(S6: Start to Acquire Infrared Fundus Image)

When the imaging start button 322 is clicked, the main controller 211 removes filters for fluorescence imaging from optical path, and turns the observation light source 11 on. Thereby, an infrared fundus image is acquired in real time. The main controller 211 may display the infrared fundus image in real time as a movie.

(S7: Specify Scan-Target Region in Infrared Fundus Image)

The scan-target region specifying part 232 specifies the image region in the infrared fundus image corresponding to the scan-target location set in Step 4. This processing is carried out successively and in real time for frames of the infrared fundus image acquired along the time series, for example. Further, an image analysis program applied to this processing may be selected according to the type of the fluorescent image.

At this stage, the main controller 211 may execute alignment and focus adjustment based on this infrared fundus image as necessary.

(S8: Display Infrared Fundus Image and Scan-Target Region)

When the specification of the scan-target region has been carried out in Step 7, the main controller 211 displays an still image based on a single frame of the infrared fundus image and information indicating the scan-target region specified for this single frame. The display mode of them may be similar to the fluorescent image G and the displayed information Q indicated in FIG. 8, for example. This is the end of preparation operation for executing OCT measurement.

(S9: Executing OCT Measurement)

The scan-target region specifying part 232 carries out matching processing between the frame (referred to as a second frame) of the infrared fundus image that is acquired at the timing corresponding to the display processing in Step 8 and the frame (referred to as a first frame) that is used in the display processing in Step 8. This matching processing is carried out by applying the aforementioned matching processing between frames. Thereby, the image region in the second frame corresponding to the scan-target region specified in the first frame is identified. This image region identified is used as the scan-target region in the second frame.

Next, the main controller 211 controls the galvano scanner 42 based on the scan-target region of the second frame to scan the signal light LS, thereby executing OCT measurement.

(S10: Form Tomographic Image)

The image forming part 220 forms a tomographic image of the fundus Ef along the scan-target region based on detection signals output from the CCD image sensor 115 while scanning the signal light LS in Step 9. The tomographic image is displayed on the display 240A by the main controller 211.

[Effects]

The effects of the fundus observation apparatus 1 are explained.

First, the fundus observation apparatus 1 displays a fluorescent image of an eye fundus previously acquired. When a scan-target location of signal light LS is set on this fluorescent image, the fundus observation apparatus 1 specifies the image region (scan-target region) in an infrared fundus image acquired by movie imaging, wherein the scan-target region corresponds to the above scan-target location, and further, the fundus observation apparatus 1 controls the galvano scanner 42 based on the scan-target region to execute OCT measurement. Then, the fundus observation apparatus 1 forms a tomographic image of the fundus Ef based on the detection result of interference light obtained by the OCT measurement.

The fundus observation apparatus 1 is configured to analyze the fluorescent image to specify a lesion candidate site of the fundus Ef, and carry out setting of the scan-target location based on the lesion candidate site.

Further, the fundus observation apparatus 1 stores analysis programs corresponding to types of fluorescent images in advance. Further, the fundus observation apparatus 1 specifies the type of the fluorescent image displayed on the display 240A, and selects the analysis program corresponding to the specified type from among the analysis programs stored in advance. Then, the fundus observation apparatus 1 specifies a lesion candidate site by analyzing the fluorescent image using the selected analysis program.

Further, the fundus observation apparatus 1 stores image analysis programs corresponding to types of fluorescent images in advance. Further, the fundus observation apparatus 1 specifies the type of the fluorescent image displayed on the display 240A, and selects the image analysis program corresponding to the specified type from among the image analysis programs stored in advance. Then, the fundus observation apparatus 1 uses the selected image analysis program to carry out image matching processing between the fluorescent image and infrared fundus image, and specifies, as the scan-target region, the image region in the infrared fundus image associated to the scan-target location in the fluorescent image by the image matching processing.

The types of fluorescent images include a first type obtained from imaging with a fluorescent agent and a second type obtained from imaging without a fluorescent agent.

In the processing of specifying the type of the fluorescent image, based on the brightness of a characteristic site of the fundus Ef in the fluorescent image displayed on the display 240A, the fundus observation apparatus 1 specifies the type of this fluorescent image.

In the case in which the fluorescent image is associated with predetermined identification information indicating the type thereof in advance, the fundus observation apparatus 1 is capable of specifying the type of the fluorescent image based on this identification information.

The fundus observation apparatus 1 comprises operation part configured to receive an operation for setting the scan-target location. The operation part comprises the operation part 240B (pointing device) and a GUI displayed on the display 240A. Further, the operation part comprises a first operation part configured to receive an operation for translating the scan-target location and a second operation part configured to receive an operation for rotating the scan-target location.

When the scan-target region corresponding to the scan-target location is specified, the fundus observation apparatus displays a still image based on a single frame of the infrared fundus image and information indicating the scan-target region specified for this single frame on the display 240A.

Further, after displaying the still image and the above information, the fundus observation apparatus 1 carries out matching processing between a new frame of the infrared fundus image obtained at the timing corresponding to this display processing and the above single frame, thereby specifying the image region in the new frame corresponding to the scan-target region specified in the single frame. Then, the fundus observation apparatus 1 controls the galvano scanner 42 based on the image region in the new frame to scan the signal light LS, thereby carrying out OCT measurement.

According to such configured fundus observation apparatus 1, it is possible to specify the scan-target region in the infrared fundus image corresponding to the scan-target location set in the fluorescent image, and carry out OCT measurement by scanning the signal light LS based on this scan-target region. In particular, the scan-target location may be set based on an abnormal site (lesion candidate site) comprehended from a fluorescent image. Therefore, it is possible to easily carry out OCT measurement of the abnormal site comprehended from a fluorescent image.

Second Embodiment

In the first embodiment, a scan-target location set on a fluorescent image acquired in the past is applied to OCT measurement in this time via an infrared fundus image acquired in real time. On contrary to this, in the second embodiment, the case in which past information other than a fluorescent image and/or a fundus image other than an infrared fundus image are/is used is explained.

Past information other than a fluorescent image is referred to as distribution information. The distribution information is information expressing distribution of examination results in over a fundus obtained by an examination performed in the past. As described above, examinations include imaging and measurement.

Images acquired by "imaging" include, in addition to a fluorescent image described in the first embodiment, an infrared image, red-free image, color fundus image, SLO image, tomographic image and three-dimensional image from OCT, projection image, shadowgram, for example. The infrared image is an image obtained by photographing using light of infrared wavelength band (by infrared photography), and includes both of a frame obtained by movie imaging and a still image obtained by still imaging. The red-free image is an image obtained by photographing using visible light of wavelength band in which red components are removed. The projection image is a front image of a fundus obtained by projecting a three-dimensional image acquired by OCT in the z-direction. The shadowgram is a front image of a fundus obtained by projecting part of the depth region of a three-dimensional image (for example, the depth region between a preset first layer and a preset second layer) acquired by OCT in the z-direction. An image obtained by photographing a fundus is constructed by multiple pixels to each of which positional information (coordinates) in the fundus and a pixel value (brightness value, RGB values, etc.) are assigned. In other words, an image is distribution information in which pixel values correspond to the abovementioned examination results.

On the other hand, "measurement" is an examination for obtaining distribution of measured values over a fundus. Such measurements include, for example, visual field test (perimetry), SLO microperimetry for measuring retinal sensitivity, layer thickness measurement for measuring the thickness of a layer in a fundus using OCT or nerve-fiver-layer analyzing apparatus. It should be noted that visual field test is explained in Japanese Unexamined Patent Application Publication No. 2009-34480 etc., SLO microperimetry is explained in Japanese Unexamined Patent Application Publication No. 2003-235800 etc., and layer thickness measurement is explained in Japanese Unexamined Patent Application Publication No. 2009-34480 etc. Measurement result information obtained by such measurements is information in which a measured value is assigned to each of positional information (coordinates) over a fundus. In other words, measurement result information is distribution information in which measured values corresponds to the abovementioned examination results.

When an infrared image or red-free image is used as distribution information, it is possible, as the case of a fluorescent image in the first embodiment, to carry out scanning of signal light based on a scan-target location set on the infrared image or red-free image.

When an color fundus image, SLO image, projection image or shadowgram is used as distribution information, since each of these images depicts morphology seen from the front side (cornea side), it is possible, as the case of a fluorescent image in the first embodiment, to carry out scanning of signal light based on a scan-target location set on the concerned image.

When a tomographic image or three-dimensional image by OCT (OCT image) is used as distribution information, it is possible to configure to specify the image region corresponding to the surface of the fundus (fundus surface region), and carry out image matching processing between this fundus surface region and infrared fundus image. Thereby, it is possible, as the first embodiment, to carry out scanning of signal light based on a scan-target location set on the OCT image.

Further, when an image acquired by scanning a fundus such as an SLO image or OCT image (scan image) is used as distribution information, based on scan position information indicating scan positions of light in this scanning (for example, information indicating directions of galvano scanner previously associated with pixel positions in advance: information indicating fixation position may be used as necessary), image matching processing between this scan image and infrared image may be carried out. Thereby, it is possible, as the first embodiment, to carry out scanning of signal light based on a scan-target location set on the scan image.

In the above examples, position matching processing between an infrared image acquired in real time and distribution information acquired in the past is carried out; however, it is possible to carry out position matching processing between distribution information and an image other than an infrared image. In other words, an image applied to this position matching processing may be an image of a fundus (simply referred to as a fundus image) that is capable of position matching with an OCT image acquired by OCT carried out in succession or in parallel. It may be a front image, or may be a tomographic image or three-dimensional image. In the case of a front image, it is possible to carry out position matching processing with distribution information as the above example. In the case of a tomographic image or three-dimensional image, it is possible to carry out position matching processing with distribution information by specifying the fundus surface region in real time as above.

In the above examples, a fundus image acquired in real time and distribution information acquired in the past are directly position-matched; however, configuration is possible in which these are position-matched via another image of the fundus.

For example, when the type of a fundus image and the type of distribution information are different, there is a risk that the precision and/or accuracy of position matching are deteriorated. In this case, it is possible to carry out position matching processing through the medium of an image that is of different type from a fundus image and is capable of position matching with distribution information (or has already been position-matched with distribution information). As a specific example of this, there is the case in which an infrared fundus image (or red-free image) is used as a fundus image and an image of other type or measurement result information is used as distribution information.

It should be noted that when measurement result information is used as distribution information, since the measurement result information expresses distribution of measured values, an image of the fundus is acquired together with measurement result information in general. By using an infrared fundus image (or red-free image) as this image of the fundus, position matching processing between infrared fundus images (or between red-free images) becomes possible. Alternatively, it is possible to select the type of a fundus image acquired in real time in accordance with the type of the image acquired together with an image of other type or measurement result information. Here, an image that is a mediator of position matching is stored in the storage 212, for example. In this case, the storage 212 functions as an example of "image storage". It should be noted that the image storage may be provided in a storage device outside the fundus observation apparatus. Such an external storage device may be a storage device mounted in a computer connected to the fundus observation apparatus, a storage device connected to the fundus observation apparatus or this computer directly or via a network.

A fundus observation apparatus which is capable of carrying out position matching via an image of other type or an image obtained together with measurement result information is explained. This fundus observation apparatus comprises a configuration illustrated in FIGS. 1 to 3 (and FIG. 4 as necessary) as the first embodiment, for example. It should be noted that the symbols used in the first embodiment is arbitrarily applied to this embodiment.

In this example, the storage 212 stores distribution information and image of the fundus Ef acquired together with this distribution information (for example, a frame of an infrared fundus image: referred to as a supplementary image).

It should be noted that the supplementary image may be an image other than an infrared image or red-free image. For example, an OCT image may be treated as the supplementary image by carrying out position matching processing between measurement result information obtained from visual field test and the OCT image using technology disclosed in Japanese Unexamined Patent Application Publication No. 2009-34480 etc. Further, an SLO image may be treated as the supplementary image by carrying out position matching processing between measurement result information obtained from SLO microperimetry and the SLO image using technology disclosed in Japanese Unexamined Patent Application Publication No. 2003-235800 etc. Moreover, an OCT image may be treated as the supplementary image by carrying out position matching processing between measurement result information obtained from layer thickness measurement through OCT and the OCT image using technology disclosed in Japanese Unexamined Patent Application Publication No. 2009-34480 etc.

Figure 9:
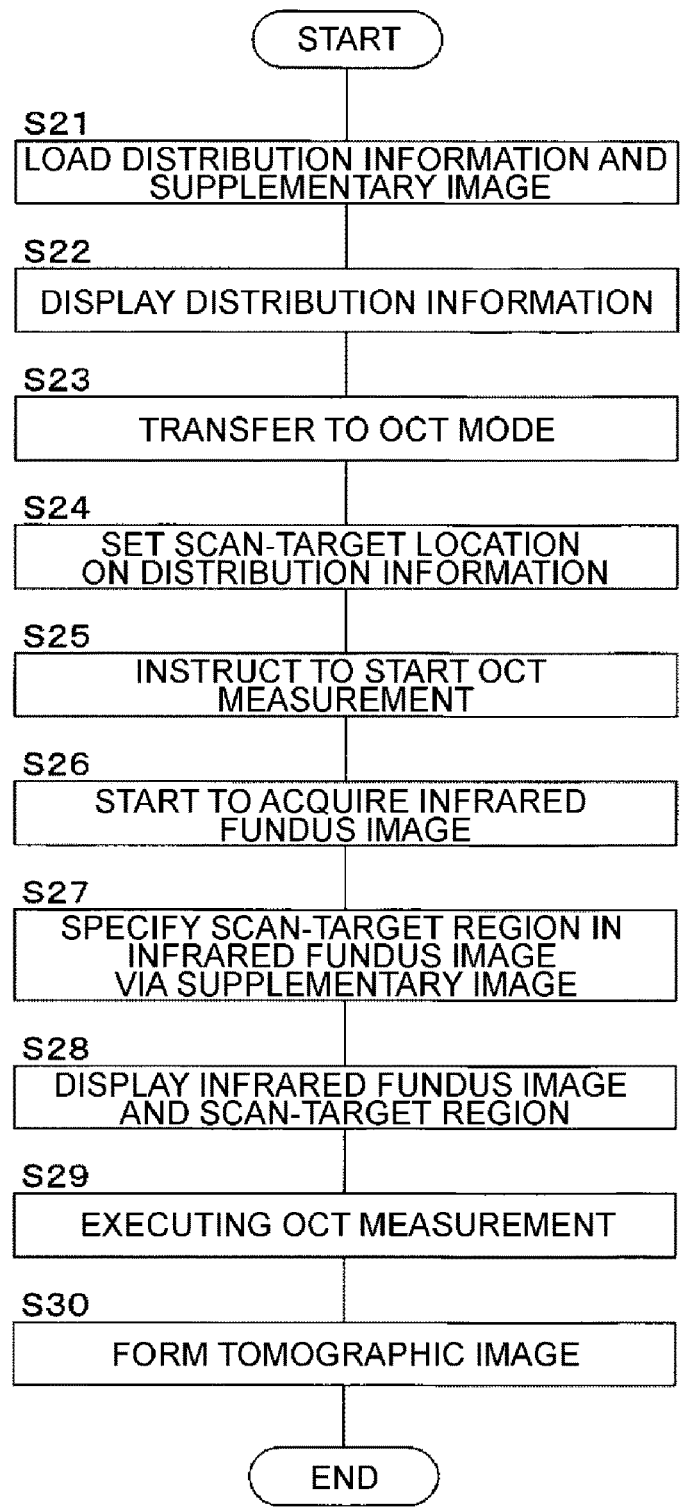
FIG. 9 is a flowchart showing an example of an operation of a fundus observation apparatus according to an embodiment.

The flowchart of FIG. 9 is referred to.

(S21: Load Distribution Information and Supplementary Image)

The main controller 211 loads distribution information and supplementary image from the storage 212.

(S22: Display Distribution Information)

The main controller 211 displays the distribution information loaded in Step 21 on the display 240A. The distribution information is displayed on a predetermined display screen. This display screen is provided with a GUI part similar to the first embodiment, for example.

When the distribution information is in particular measurement result information, the main controller 211 may display the measurement result information over the supplementary image. Thereby, it becomes possible to easily comprehend the positional relationship between the supplementary image that is an image of the fundus and the measurement result information that expresses distribution of measured values. In other words, it becomes possible to intuitively comprehend how measured values distribute over the fundus Ef. By applying such overlay processing, it is possible to facilitate manual setting of the scan-target location in Step 24.

(S23: Transfer to OCT Mode)

The user manipulates the GUI part to instruct translation to the OCT mode. The main controller 211 receives this instruction and changes the displayed contents of the GUI part as the first embodiment, for example. After the displayed contents are changed, an imaging start button, translation button, rotation button etc. are displayed in the GUI part.

(S24: Set Scan-Target Location on Distribution Information)

The scan-target location setting part 231 sets a scan-target location on the distribution information displayed. This setting processing is carried out automatically or manually as the first embodiment, for example.

(S25: Instruct to Start OCT Measurement)

When the setting of the scan-target location is completed, the user manipulates the GUI part to instruct to start OCT measurement. Upon receiving this instruction, the main controller 211 starts preparation operation of OCT measurement as stated below.

(S26: Start to Acquire Infrared Fundus Image)

Upon receiving the instruction of starting OCT measurement, the main controller 211 turns the observation light source 11 on. Thereby, an infrared fundus image is acquired in real time. The main controller 211 may display the infrared fundus image in real time as a movie.

(S27: Specify Scan-Target Region in Infrared Fundus Image Via Supplementary Image)

The scan-target region specifying part 232 specifies the image region in the supplementary image corresponding to the scan-target location set on distribution information in Step 24. This processing is carried out, for example, based on the association of positions having already been performed between the distribution information and the supplementary image. Further, the scan-target region specifying part 232 specifies the image region in the infrared fundus image corresponding to the image region in the supplementary image. This processing is carried out between the respective frame of the infrared fundus image acquired in time series and the supplementary image successively and in real time. Here, it is possible to select an image analysis program used in this processing in accordance with the type of the supplementary image.

At this stage, the main controller 211 may carry out alignment and focus adjustment based on this infrared fundus image as necessary.

(S28: Display Infrared Fundus Image and Scan-Target Region)

When the specification of the scan-target region in Step 27 is done, the main controller 211 displays a still image based on a single frame of the infrared fundus image and information indicating the scan-target region specified for this single frame. The display mode thereof is the same as the first embodiment, for example. This is the end of preparation operation for carrying out OCT measurement.

(S29: Executing OCT Measurement)

The scan-target region specifying part 232 carries out matching processing between the frame (referred to as a second frame) of the infrared fundus image that is acquired at the timing corresponding to the display processing in Step 28 and the frame (referred to as a first frame) that is used in the display processing in Step 28. This matching processing is carried out by applying the matching processing between frames as explained in the first embodiment, for example. Thereby, the image region in the second frame corresponding to the scan-target region specified in the first frame is identified. This image region identified is used as the scan-target region in the second frame.

Next, the main controller 211 controls the galvano scanner 42 based on the scan-target region of the second frame to scan the signal light LS, thereby executing OCT measurement.

(S30: Form Tomographic Image)

The image forming part 220 forms a tomographic image of the fundus Ef along the scan-target region based on detection signals output from the CCD image sensor 115 while scanning the signal light LS in Step 29. The tomographic image is displayed on the display 240A by the main controller 211. This is the end of the present operation example.

Effects of the fundus observation apparatus according to the present embodiment are explained.

In the present embodiment, distribution information is an arbitrary image or measurement result information of a fundus. Further, a supplementary image acquired together with the distribution information is stored in an image storage such as the storage 212. Here, the abovementioned arbitrary image and supplementary image are images of different types from each other, for example.

The scan-target location setting part 231 sets a scan-target location on the distribute information displayed on the display 240A. The scan-target location setting part 231 specifies the image region in the supplementary image corresponding to the scan-target location set on the distribution information, and further specifies the image region in the fundus image corresponding to this image region in the supplementary image. This fundus image is, for example, a moving image acquired by the fundus observation apparatus in real time (for example, an infrared fundus image, red-free image, SLO image, etc.).

The main controller 211 controls the galvano scanner 42 based on the image region in the fundus image specified by the scan-target region specifying part 232 to scan the signal light LS. The image forming part 220 forms a tomographic image based on the detection results of the interference light LC while scanning the signal light LS based on this control.

According to the fundus observation apparatus that acts in such a way, it is possible to transfer the scan-target location set on the distribution information to a real-time fundus image through the medium of the supplementary image acquired together with the distribution information, and carry out OCT measurement of the scan-target region specified in the transferring processing. Therefore, it is possible to easily carry out OCT measurement of a characteristic site obtained from distribution information of arbitrary type.

Further, by matching the type of the supplementary image and the type of the real-time fundus image (or by setting the type of the supplementary image and the type of the real-time fundus image to the combination of types in which position matching such as image matching can be carried out with relatively high accuracy and high precision), OCT measurement of the characteristic site may be carried out with high accuracy and high precision.

Third Embodiment

In the present embodiment, examples of user interfaces that can be used in combination with the first and/or second embodiments are explained. The symbols used in the above embodiments are arbitrarily applied to the following explanation.

Figure 10:
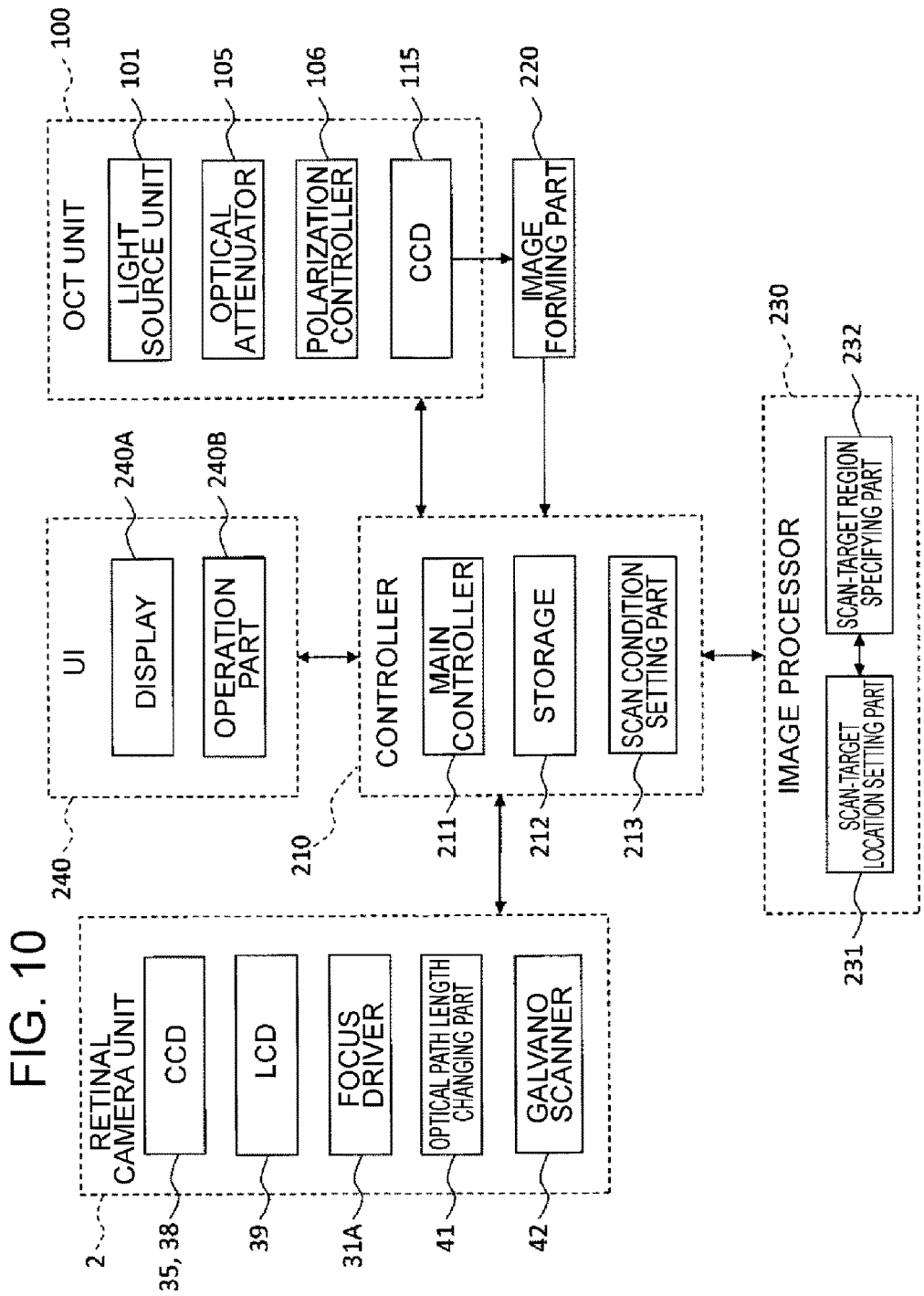
FIG. 10 is a schematic block diagram showing an example of a configuration of a fundus observation apparatus according to an embodiment.

FIG. 10 illustrates an example of a configuration of a fundus observation apparatus according to the present embodiment. This fundus observation apparatus comprises almost the same configuration as the first embodiment. The difference is that a scan condition setting part 213 is provided in the controller 210. The main controller 211 in the present embodiment functions as an example of "display controller". Aspects of operations of the scan condition setting part 213 and the main controller 211 are explained later.

Figure 11:
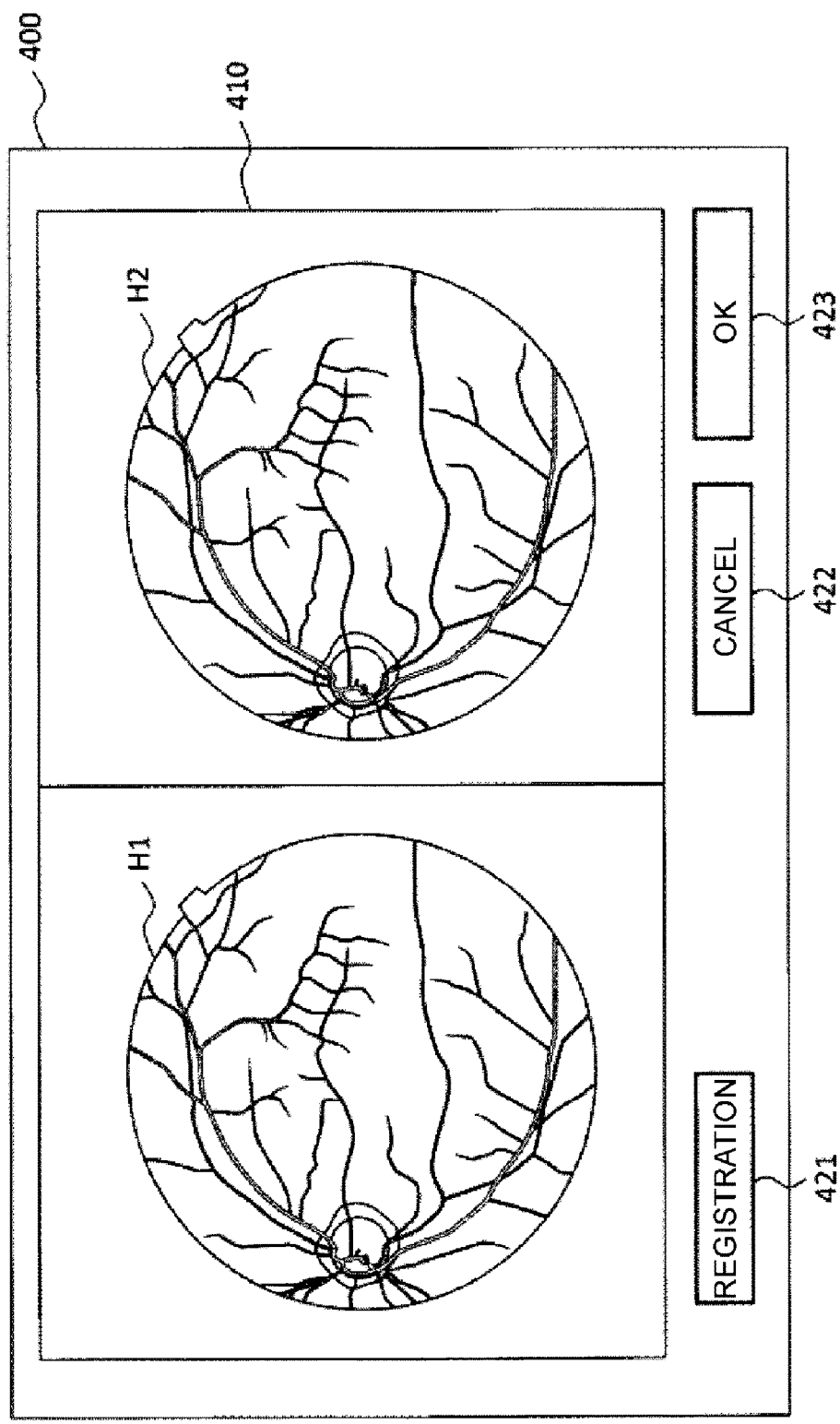
FIG. 11 is a schematic diagram for explaining an operation of a fundus observation apparatus according to an embodiment.

The main controller 211 displays a position matching screen 400 shown in FIG. 11. An image display part 410 on which two images that are subjects of position matching is provided in the position matching screen 400. A registration button 421, cancel button 422 and OK button 423 are provided below the image display part 410.

Two images displayed on the image display part 410 may be an arbitrary combination. In the following description, it is assumed that an image H1 displayed on the left is an infrared fundus image of the fundus Ef acquired by the fundus observation apparatus in real time. The aspect of displaying the infrared fundus image H1 may be a movie or still image based on a single frame. Further, it is assumed that an image H2 displayed on the right is a color fundus image of the fundus Ef acquired in the past. Hereinafter, the case is explained in which a scan-target location is set on the color fundus image of the fundus Ef acquired in the past and OCT measurement of the fundus Ef is carried out based on this scan-target location.

The user observes the infrared fundus image H1 and the color fundus image H2 and specifies at least three characteristic points of the fundus Ef. Further, the user uses the operation part 240B (pointing device such as a mouse) to designate image points corresponding to the specified three or more characteristic points on each of the infrared fundus image H1 and the color fundus image H2. The main controller 211 displays information indicating the designated image points over the respective images H1 and H2. It should be noted that examples of the characteristic points include the center or edge of an optic disc, a characteristic blood vessel, a branch point of blood vessels, a lesion site, etc.

When the discrimination of these characteristic points is difficult, enhancement processing may be carried out on the concerned image. This enhancement processing is carried out, for example, by executing two-dimensional Fourier transform or discrete cosine transform to form an image in a frequency space, and applying a high pass filter for removing only preset low frequency components in this frequency space or a band pass filter for removing preset low frequency components and preset high frequency components. It should be noted that the area of frequency components to be removed may be arbitrarily set based on low frequency components to be removed in the real space, degree of improving contrast, etc. this removal area of the frequency components may be an area set in advance, or an area set by analyzing an image in the frequency space.

Another enhancement processing may be the following. First, a smoothed image is formed by executing smoothing processing on an image. Next, a subtraction image between the smoothed image and the original image is formed. Further, an image from which low frequency components are removed is formed by composing the original image and the subtraction image. Here, it is possible to multiply the original image and/or the smoothed image by a preset weight to form a subtraction image in the subtraction processing, and divide the subtraction image by the value calculated by subtracting the weight from 1 in the composition processing. Further, this weight may be a value between 0.7 and 0.9, and a subtraction image of the smoothed image multiplied by this value and the original image may be formed in the subtraction processing. An instruction for executing enhancement processing such as the above is carried out by manipulating an enhancement processing setting part 529 (described later), for example.

Figure 12:
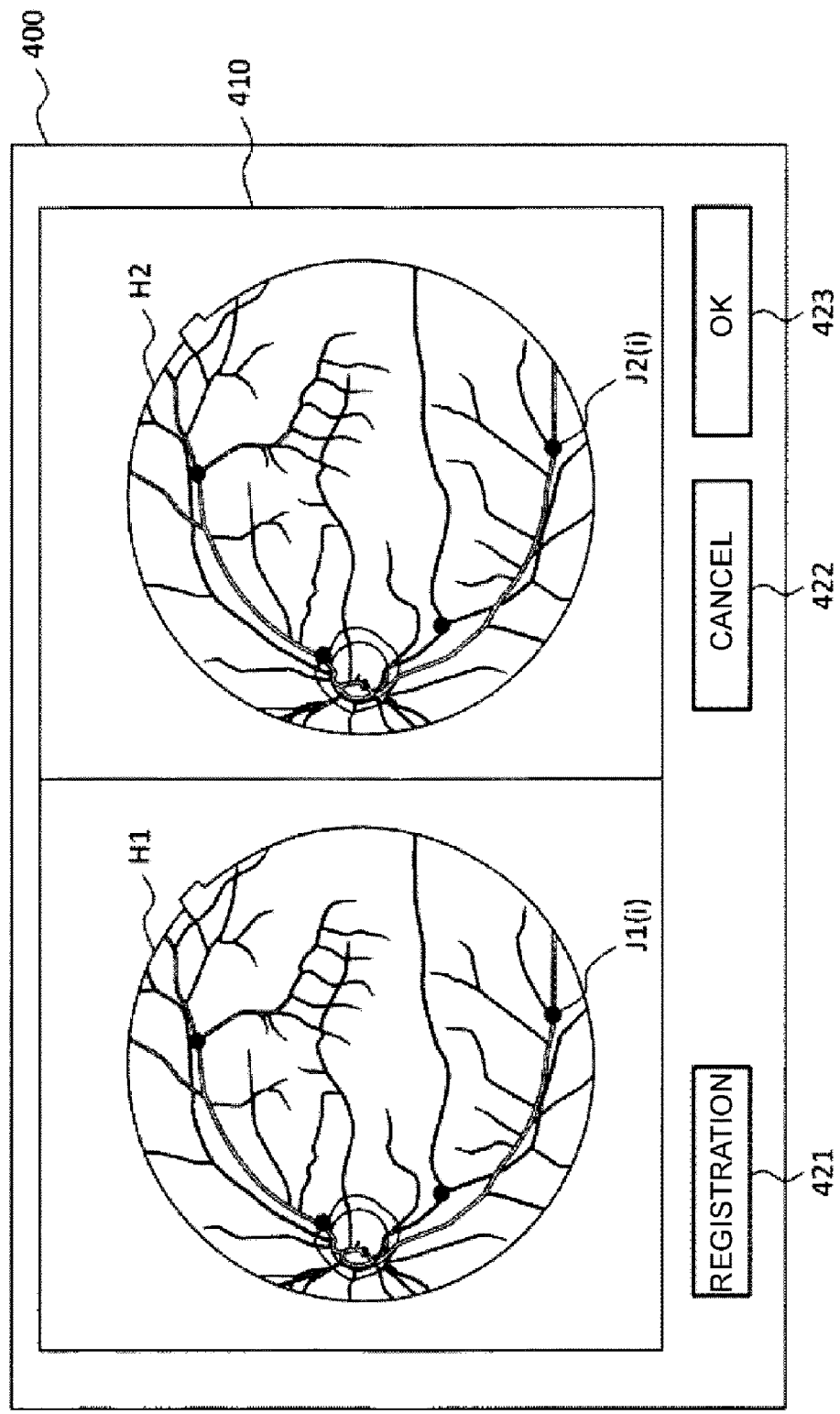
FIG. 12 is a schematic diagram for explaining an operation of a fundus observation apparatus according to an embodiment.

FIG. 12 illustrates an example of the display aspect when four characteristic points are designated on the respective images H1 and H2. In FIG. 12, the image positions of the characteristic points designated on the infrared fundus image H1 are indicated by dots J1($i$) ($i$=1 to 4). Further, the image positions of the characteristic points designated on the color fundus image H2 are indicated by dots J2($i$) ($i$=1 to 4). For each $i$=1 to 4, the dot J1($i$) and the dot J2($i$) indicate the identical characteristic point.

It should be noted that the association of characteristic points between the two images H1 and H2 may be carried out by the user or the main controller 211. In an example of the former case, the user inputs identification information for the respective characteristic points using the operation part 240B when designating the image positions of the characteristic points, and then the main controller 211 collates the multiple identification information between the two images H1 and H2, thereby obtaining the above association. In an example of the latter case, the main controller 211 associates characteristic points in the two images H1 and H2 such that they are in corresponding positions based on the positional relationship of the designated characteristic points.

When the user clicks the registration button 421 using the operation part 240B, the image processor 230 carries out position matching of the pairs of characteristic points between the two images H1 and H2, thereby performing position matching processing between the two images H1 and H2. This position matching processing associates the coordinates in the infrared fundus image H1 and the coordinates in the color fundus image H2. Therefore, in response to the designation of positions in one image of the two images H1 and H2, the position in the other image corresponding to this designated position is specified. This specification processing is carried out by the main controller 211 or the image processor 230, for example.

When the result of image registration is unsatisfactory, the user clicks the cancel button 422 through the operation part 240B. Then, the above operations are carried out again. On the other hand, when the image registration is completed, the user clicks the OK button 423 with the operation part 240B. Upon receiving this, the main controller 211 displays a scan-target location setting screen 500 shown in FIG. 13 on the display 240A.

Figure 13:
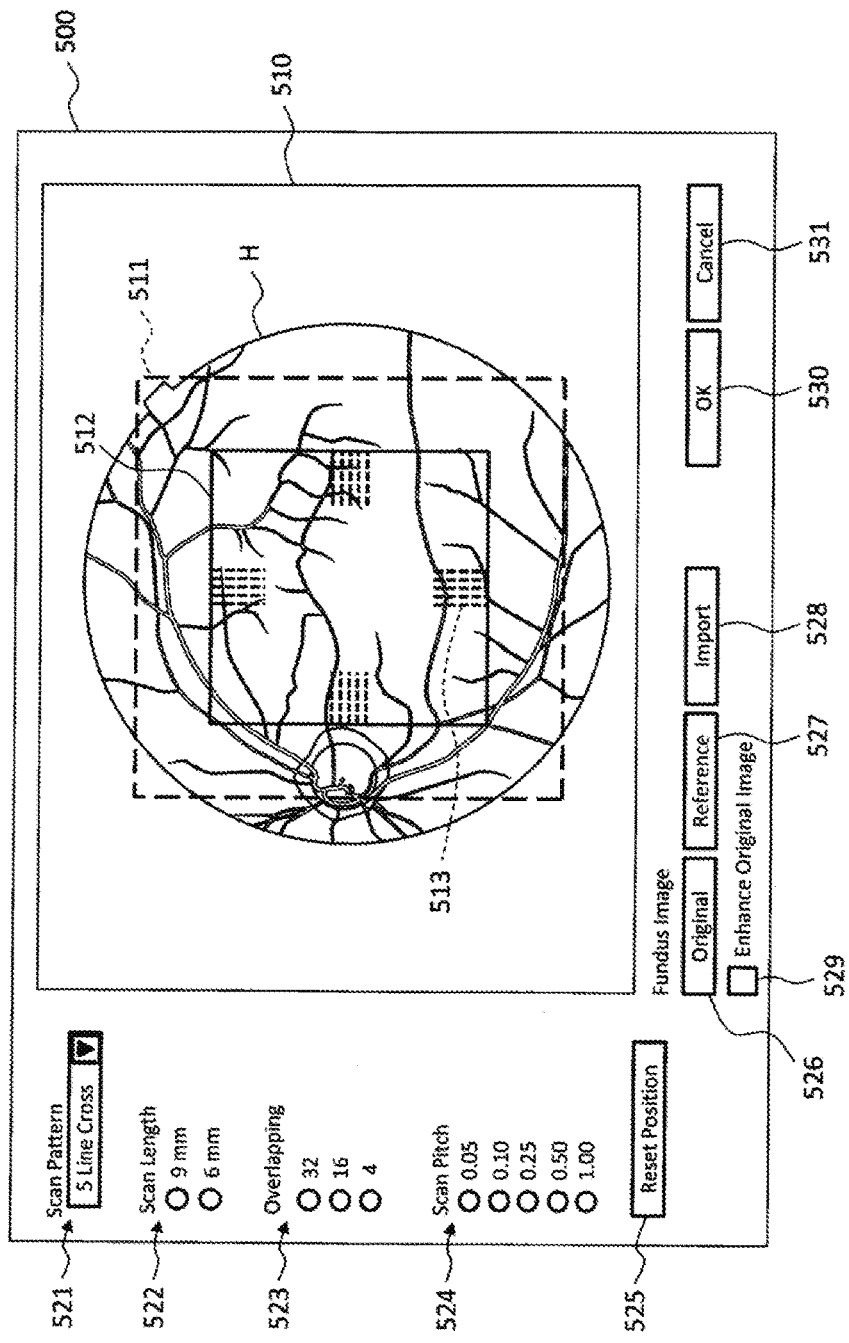
FIG. 13 is a schematic diagram for explaining an operation of a fundus observation apparatus according to an embodiment.

In the scan-target location setting screen 500, an image display part 510, scan pattern setting part 521, scan length setting part 522, averaging number setting part 523, scan pitch setting part 524, position reset button 525, original image display button 526, reference image display button 527, import image display button 528, enhancement processing setting part 529, OK button 530 and cancel button 531 are provided. An image H presented in the image display part 510 in FIG. 13 is the infrared fundus image H1 or color image H2. It should be noted that when an image other than these is processed (for example, when the supplementary image in the second embodiment is under consideration), the image H may include the concerned image.

Various kinds of images are displayed in the image display part 510. In this operation example, a mode of displaying images in the image display part 510 is assumed to be switching display. For example, when the original image display button 526 is clicked, the main controller 211 displays the infrared fundus image H1 in the image display part 510. Further, when the reference image display button 527 is clicked, the main controller 211 displays the color fundus image H2 in the image display part 510. Further, when the import image display button 528 is clicked, the main controller 211 displays an imported image (such as the supplementary image) other than these images in the image display part 510.

The scan pattern setting part 521, scan length setting part 522, averaging number setting part 523, scan pitch setting part 524, position reset button 525 are used for operation of inputting scan condition of OCT measurement. The scan condition means one or more parameters that determine the way of scanning of the signal light LS. The parameters may include scan pattern indicating the form (shape) of scanning, scan length indicating the length of scanning, averaging number (number of images overlapped) indicating the number of repetition of scanning for acquiring a single image, scan pitch indicating the interval between scan points (irradiation spots of the signal light LS), etc.

The scan pattern setting part 521 is used for setting which of various scan patterns described in the first embodiment is selectively applied. It should be noted that although the scan pattern setting part 521 illustrated in FIG. 13 is a pull-down menu, it is not limited to this. When a scan pattern is set by using the scan pattern setting part 521, the result of the setting is sent to the scan condition setting part 213.

The scan length setting part 522 is used for setting scan length. The scan length is defined in advance according to scan patterns, for example. For example, for line scan and a scan pattern consisting of a combination line scans, the length of the respective scan lines is defined as the scan length; and for circular scan, the diameter of the circular scan line is defined as the scan length. It should be noted that although the scan length setting part 522 illustrated in FIG. 13 comprises multiple check boxes as choices, it is not limited to this (the same hereinafter). When a scan length is set by using the scan length setting part 522, the result of the setting is sent to the scan condition setting part 213.

The averaging number setting part 523 is used for setting the number of repetition of scan. The signal light LS is repeatedly scanned along the same scan line(s) by the number set. The image forming part 220 averages multiple data (images) acquired along the same scan line to form a tomographic image in which random noises are reduced. When the repeating number (averaging number) is set by using the averaging number setting part 523, the result of the setting is sent to the scan condition setting part 213.

The scan pitch setting part 524 is used for setting the interval between scan points (scan pitch). When the scan pitch is set by using the scan pitch setting part 524, the result of the setting is sent to the scan condition setting part 213.

The scan condition setting part 213 (or the storage 212) previously stores information indicating choices of the respective scan conditions described above. The scan condition setting part 213 refers to this information to combine the scan conditions set as above. For example, when "5 line cross" consisting of 5 vertical line scans and 5 horizontal line scans is set for the scan pattern, "6 mm" is set for the scan length, "16" is set for the averaging number, and "0.01" is set for the scan pitch, the scan condition setting part 213 refers the above information to generate scan condition information that is the combination of these and transfers the scan condition information to the main controller 211.

Since manual input operation by the user is included in the setting of scan condition in this operation example, the scan condition setting part 213 and the user interface 240 configures "scan condition setting part". On the other hand, the setting of scan condition is automatically carried out, "scan condition setting part" may not need to include the user interface 240. This automatic setting is used in the case in which the same scan condition is applied as above such as medical follow-up and preoperative and postoperative observation, for example. Further, automatic setting is also applied when conditions such as name and/or condition of disease and scan condition are associated with each other in advance.

The main controller 211 determines contents displayed in the image display part 510 based on the scan condition information generated by the scan condition setting part 213, and displays the contents in the image display part 510. FIG. 13 illustrates an example of displaying a scannable area image 511, scan center movable area image 512 and scan pattern image 513 over the image H.

The scannable area image 511 is a frame shape image indicating the area in which scan can be performed based on the concerned scan condition. The shape of the scannable area image 511 is determined in accordance to the set content of scan pattern, and the size thereof is determined in accordance to the set content of scan length (and, possibly, the imaging angle of view of the image H and/or the display size).

The scan center movable area image 512 is a frame shape image indicating the area in which the center position of the scan can be moved for the scan based on the concerned scan condition. The shape of the scan center movable area image 512 is determined in accordance to the set content of scan pattern, and the size thereof is determined in accordance to the set content of scan length (and, possibly, the imaging angle of view of the image H and/or the display size).

The scan pattern image 513 is an image with the shape indicating the scan pattern set. It should be noted that the scan pattern image 513 is not necessarily the same shape as the scan pattern set. For example, the scan pattern image 513 in FIG. 13 shows the "5 line cross"; however, only the end parts of the "5 line cross" are presented. This is because there is a risk that observation of the image H is disturbed if parts of the "5 line cross" other than the end parts (in particular, the center part thereof) are overlaid on the image H.

The user may move the scan pattern image 513 by using the operation part 240B. This is an example of operation for changing scan position. This operation is carried out by using a pointing device such as a mouse, for example. As a specific example of this, the user carries out a drag operation while locating the pointer at a site other than a predetermined site (for example, the end parts) of the scan pattern image 513 to translate the scan pattern image 513 on the image H. Further, the user carries out a drag operation while locating the pointer at the predetermined site of the scan pattern image 513 to rotate the scan pattern image 513 on the image H. the rotation center at the time is an arbitrary position on the scan pattern image 513, or a position designated on the image H in advance. Further, the user clicks an arbitrary position on the image H to move the scan pattern image 513 such that the center position of the scan is located at this clicked position.

It should be noted that the scannable area image 511 is not necessarily displayed at all times. For example, it is configured that when the operation is performed for setting the scan-target location in the external region of the area being defined by the scannable area image 511, the main controller 211 overlays the scannable area image 511. Similar control may be applied to the case in which the scan-target location is set such that the scan center is located in the external region of the scan center movable area image 512. Such display control is carried out based on the fact that the association between the scannable area or scan center movable area and the image H is already obtained.

Further, it is also configured that when the operation is performed for setting the scan-target location in the external region of the area being defined by the scannable area image 511, the main controller 211 moves and overlays the scannable area image 511 in the internal region of this scannable region. Similar control may be applied to the case in which the scan-target location is set such that the scan center is located in the external region of the scan center movable area image 512. In such processing, the moving destination of the scan-target location is determined arbitrarily. For example, the moving destination of the set scan-target location may be the position that is on the line segment connecting a preset reference position (such as the center position of the image H) and the position set as the scan-target location, and that belongs to the internal region the concerned scannable area (or the concerned scan center movable area).

The position reset button 525 is used for resetting such manual changes of the scan-target location and returning the scan-target location to a preset default location.

As described above, the user sets the scan-target location by referring to the image H. In particular, it is possible to carry out the setting of the scan-target location by referring to the color image H2 of the fundus Ef acquired in the past.

When an instruction to display the infrared fundus image H1 by clicking the original image display button 526 after completing the setting of the scan-target location on the color image H2, the scan-target region specifying part 232 changes the scan-target location (the location of the scan pattern image 513) set on the color image H2 based on the result of the abovementioned image matching, thereby specifying the image region in the infrared fundus image H1 corresponding to the set scan-target location.

The main controller 211 displays the infrared fundus image H1 in the image display part 510 and displays the scan pattern image 513 over the specified image region. At this time, the positions of the scannable area image 511 and scan center movable area image 512 displayed over the infrared fundus image H1 are also changed based on the result of the image matching. In other words, according to this operation example, in response to switching of the image displayed, the display positions of the scannable area image 511, scan center movable area image 512 and scan pattern image 513 may be changed according to the position shift between images.

The main controller 211 receives a predetermined trigger, and carries out OCT measurement with the scan condition corresponding to the scan pattern image 513 on the infrared fundus image H1 (and each scan condition of the averaging number and scan pitch).

The above is an explanation of the case in which distribution information is an image; however, similar processing may be carried out in the case in which distribution information is measurement result information. In such cases, the scan-target location set on the measurement result information may be transferred to an infrared fundus image (real-time fundus image) through the medium of a supplementary image, as described in the second embodiment. At this time, the supplementary image and infrared fundus image are displayed side-by-side in the image display part 510 of the position matching screen 400 illustrated in FIG. 11.

Further, the main controller 211 may display the measurement result information over the supplementary image based on the known positional relationship between the supplementary image and the measurement result information. Thus, it becomes possible to easily comprehend the location of the measurement result information in the supplementary image (that is, the location of the measurement result information on the fundus Ef), thereby facilitating the setting of the scan-target location.

Further, the main controller 211 may display the measurement result information over the infrared fundus image based on the above positional relationship and the result of the above position matching. Thus, it becomes possible to easily comprehend the location of the measurement result information in a fundus image acquired in real time, that is, the location of the measurement result information on the fundus Ef currently observed.

Effects of the fundus observation apparatus according to the present embodiment are explained.

The fundus observation apparatus is capable of displaying, over distribution information, settable area information indicating an area in which the scan-target location may be set (settable area). This settable area information is the scannable area image 511 or scan center movable area image 512, for example. Thus, setting operation of the scan-target location may be assisted. Further, it is possible to avoid errors in setting the scan-target location.

Further, the settable area information is not necessarily displayed at all times. For example, it is possible to display the settable area information over the distribution information in response to the execution of an operation for setting the scan-target location in the external region of the settable area in the distribution information. Thus, observation of the distribution information is preferably performed, and when the setting of the scan-target location is inappropriate, the apparatus is capable of informing this fact to the user.

Further, this fundus observation apparatus comprises the scan condition setting part 213 that sets scan condition of the signal light LS together with the configuration of the above embodiment. Moreover, the main controller 211 (display controller) of this fundus observation apparatus is capable of switching the morphology of the settable area information displayed over the distribution information in accordance with the result of setting of the scan condition. Thus, the settable area information with morphology according to the result of setting of the scan condition is displayed over the distribution information, and therefore it becomes possible to preferably assist the setting of the scan-target location.

Moreover, when an operation for setting the scan-target location in the external region of the settable area in the distribution information is carried out, the scan-target region specifying part 232 can set new scan-target location in the internal region of this settable area. Thus, even though the scan-target location is set at an inappropriate location, new scan-target location may be automatically set at an appropriate location, thereby preferably assisting the setting of scan-target location. It should be noted that it is also possible to determine new scan-target location taking into account the scan-target location set by the user.

Further, this fundus observation apparatus is capable of displaying measurement result information over a supplementary image. Thus, the setting of the scan-target location may be preferably assisted. Moreover, this fundus observation apparatus is capable of displaying measurement result information over a fundus image (infrared fundus image etc.). Thereby, it is possible to easily comprehend the location of the measurement result information in the fundus Ef currently observed.

When OCT measurement is carried out through the above processing, arbitrary combination of images from among an OCT image acquired by this OCT measurement, distribution information (image, measurement result information), supplementary image, and real-time fundus image are displayed side-by-side.

Modification Example

The configuration described above is merely one example for favorably implementing the present invention. Therefore, it is possible to appropriately make arbitrary modification (omission, replacement, addition, etc.) within the scope of the present invention.

In the above embodiment, the optical path length difference between the optical path of the signal light LS and the optical path of the reference light LR is changed by varying the position of the optical path length changing part 41; however, a method for changing the optical path length difference is not limited to this. For example, it is possible to change the optical path length difference by providing a reference mirror (reference mirror) in the optical path of the reference light and moving the reference mirror in the advancing direction of the reference light to change the optical path length of the reference light. Further, the optical path length difference may be changed by moving the retinal camera unit 2 and/or the OCT unit 100 with respect to the eye E to change the optical path length of the signal light LS. Moreover, in a case that an object is not a living site or the like, it is also effective to change the optical path length difference by moving the object in the depth direction (z-direction).

Computer programs for implementing the above embodiments can be stored in any kind of recording medium that can be read by a computer. As such recording media, for example, an optical disk, a semiconductor memory, a magneto-optic disk (CD-ROM, DVD-RAM, DVD-ROM, MO, and so on), and a magnetic storage (a hard disk, a Floppy Disk™, ZIP, and so on) can be used.

In addition, it is possible to transmit/receive this program through a network such as internet or LAN etc.

EXPLANATION OF SYMBOLS 1 fundus observation apparatus
2 retinal camera unit
10 illumination optical system
30 imaging optical system
31 focusing lens
31A focus driver
41 optical path length changing part
42 galvano scanner
50 alignment optical system
60 focus optical system
100 OCT unit
101 light source unit
105 optical attenuator
106 polarization controller
115 CCD image sensor
200 arithmetic and control unit
210 controller
211 main controller
212 storage
213 scan condition setting part
220 image forming part
230 image processor
231 scan-target location setting part
2311 lesion candidate site specifying part
2312 program storage
2313 type specifying part
2314 program selecting part
2315 fluorescent image analyzer
2316 setting processor
232 scan-target region specifying part
240A display
240B operation part
E eye
Ef (eye) fundus
LS signal light
LR reference light
LC interference light

What is claimed is:

1. A fundus observation apparatus, comprising:
    a display configured to display a fluorescent image of examination results of an eye fundus acquired by examination carried out in the past;
    an imaging optic configured to carry out movie imaging of the eye fundus;
    a tomographic imager comprising an optical system that generates and detects interference light by superposing signal light returned from the eye fundus on reference light, and a scanner that scans the eye fundus with the signal light, and further configured to form a tomographic image of the eye fundus based on the detection results of the interference light acquired by the scanning;
    a setting part included within at least one processor including circuitry and configured to specify a site by executing analysis processing in accordance with whether the fluorescent image was captured by applying a fluorescent agent or captured without applying the fluorescent agent and configured to set a scan-target location of the signal light on the fluorescent image displayed on the display based on the specified site;
    a specifying part included within said at least one processor including circuitry and configured to specify regions, within a fundus image obtained by the movie imaging, that corresponds to the scan-target location to be scanned by the scanner of the tomographic imager by carrying out image matching in accordance with whether the fluorescent image was captured by applying the fluorescent agent or captured without applying the fluorescent agent between the displayed image and the fundus image to identify the regions within the fundus image, and
    a programmed controller configured to control the scanner based on the specified image region to carry out the scanning of the signal light across the regions within the fundus image,
    wherein the tomographic imager forms a tomographic image from the detection results of the interference light acquired by the scanning of the signal light across the regions within the fundus image.

2. The fundus observation apparatus of claim 1, wherein the setting part comprises an analyzer configured to analyze the fluorescent image to specify a lesion candidate site in the eye fundus, and sets the scan-target location based on the specified lesion candidate site.

3. The fundus observation apparatus of claim 2, wherein the analyzer comprises:
    a first storage configured to previously store two or more analysis programs, each corresponding to fluorescent images captured by applying the fluorescent agent or to fluorescent images captured without applying the fluorescent agent;
    a first type specifying part included within said at least one processor including circuitry and configured to specify whether the fluorescent image displayed on the display was captured by applying the fluorescent agent or captured without applying the fluorescent agent; and
    a first selecting part included within said at least one processor including circuitry and configured to select an analysis program corresponding to whether the fluorescent image was captured by applying the fluorescent agent or captured without applying the fluorescent agent from among the two or more analysis programs, and
    the analyzer analyzes the fluorescent image with the selected analysis program to specify the lesion candidate site.

4. The fundus observation apparatus of claim 3, wherein the first type specifying part specifies whether the fluorescent image was captured by applying the fluorescent agent or captured without applying the fluorescent agent based on the examination result of a characteristic site of the eye fundus in the displayed fluorescent image.

5. The fundus observation apparatus of claim 3, wherein the displayed fluorescent image is associated with preset identification information indicating in advance whether the fluorescent image was captured by applying the fluorescent agent or captured without applying the fluorescent agent, and the first type specifying part specifies whether the fluorescent image was captured by applying the fluorescent agent or captured without applying the fluorescent agent based on the identification information.

6. The fundus observation apparatus of claim 3, wherein the fluorescent image includes a fluorescent image of the eye fundus in which pixel values correspond to the examination results.

7. The fundus observation apparatus of claim 1, wherein the setting part comprises an operation part included within said at least one processor including circuitry and configured to receive an operation for setting the scan-target location.

8. The fundus observation apparatus of claim 7, wherein the display displays, over the fluorescent image, settable area information indicating an area in which the scan-target location may be set.

9. The fundus observation apparatus of claim 8, further comprising:
   a scan condition setting included within said at least one processor including circuitry and configured to set a scan condition of the signal light; and
   a programmed display controller configured to switch the form of the settable area information displayed over the fluorescent image depending on the setting result of the scan condition.

10. The fundus observation apparatus of claim 8, wherein when an operation for setting the scan-target location inside an external region of the area in the fluorescent image is carried out, the setting part sets a new scan-target location inside an internal region of the area.

11. The fundus observation apparatus of claim 7, wherein the operation part comprises at least one of a pointing device and a graphical user interface.

* * * * *